United States Patent
Yodfat et al.

(10) Patent No.: US 10,398,831 B2
(45) Date of Patent: *Sep. 3, 2019

(54) POSITIVE DISPLACEMENT PUMP

(71) Applicant: Roche Diabetes Care, Inc., Indianapolis, IN (US)

(72) Inventors: Ofer Yodfat, Maccabim-Reut (IL); Avraham Neta, Misgav (IL); Yossi Shalev, Karkor (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 587 days.

This patent is subject to a terminal disclaimer.

(21) Appl. No.: 14/826,804

(22) Filed: Aug. 14, 2015

(65) Prior Publication Data
US 2015/0352276 A1      Dec. 10, 2015

Related U.S. Application Data

(63) Continuation of application No. 12/451,435, filed as application No. PCT/IL2008/000641 on May 11, 2008, now Pat. No. 9,138,534.
(Continued)

(51) Int. Cl.
*A61M 5/142*      (2006.01)
*A61M 5/172*      (2006.01)
(Continued)

(52) U.S. Cl.
CPC ...... *A61M 5/14248* (2013.01); *A61M 5/1452* (2013.01); *A61M 5/172* (2013.01); *F04B 43/1269* (2013.01); *A61M 5/148* (2013.01); *A61M 5/14232* (2013.01); *A61M 2005/14208* (2013.01); *A61M 2005/14252* (2013.01); *A61M 2005/14268* (2013.01);
(Continued)

(58) Field of Classification Search
CPC ................ A61M 5/14248; A61M 2005/14268
See application file for complete search history.

(56) References Cited

U.S. PATENT DOCUMENTS

| 3,631,847 A | 1/1972 | Hobbs, II |
| 3,771,694 A | 11/1973 | Kaminski |

(Continued)

FOREIGN PATENT DOCUMENTS

| WO | 8203556 A1 | 10/1982 |
| WO | 8500523 A1 | 2/1985 |

(Continued)

OTHER PUBLICATIONS

U.S. Appl. No. 11/989,684, filed Jan. 28, 2008, Yodfat et al. (now U.S. Pat. No. 8,696,570 B2).
(Continued)

*Primary Examiner* — Laura A Bouchelle
(74) *Attorney, Agent, or Firm* — Dinsmore & Shohl, LLP

(57) ABSTRACT

Systems, methods and apparatuses for delivering therapeutic fluid to the body of a patient are disclosed. The apparatus includes a dispensing unit having a driving mechanism, a pumping mechanism, a reservoir containing therapeutic fluid, and an outlet port. The driving mechanism causes the pumping mechanism to positively displace therapeutic fluid within the reservoir for delivery of therapeutic fluid to the body of the patient via the outlet port.

19 Claims, 34 Drawing Sheets

Related U.S. Application Data

(60) Provisional application No. 60/928,750, filed on May 11, 2007, provisional application No. 60/928,751, filed on May 11, 2007, provisional application No. 60/928,815, filed on May 11, 2007.

(51) Int. Cl.
    *A61M 5/145*         (2006.01)
    *F04B 43/12*         (2006.01)
    *A61M 5/148*         (2006.01)

(52) U.S. Cl.
    CPC ........... *A61M 2202/0007* (2013.01); *A61M 2205/3569* (2013.01); *A61M 2205/3592* (2013.01); *A61M 2210/04* (2013.01)

(56) References Cited

U.S. PATENT DOCUMENTS

| | | | |
|---|---|---|---|
| 3,858,581 A | 1/1975 | Kamen | |
| 4,435,173 A | 3/1984 | Siposs et al. | |
| 4,498,843 A | 2/1985 | Schneider et al. | |
| 4,544,369 A | 10/1985 | Skakoon et al. | |
| 4,552,561 A * | 11/1985 | Eckenhoff | A61M 5/14248 424/449 |
| 4,652,260 A | 3/1987 | Fenton, Jr. et al. | |
| 4,657,486 A | 4/1987 | Stempfle et al. | |
| 4,715,786 A | 12/1987 | Wolff et al. | |
| 5,322,511 A | 6/1994 | Armbruster et al. | |
| 5,954,697 A | 9/1999 | Srisathapat et al. | |
| 5,957,895 A | 9/1999 | Sage et al. | |
| 6,485,461 B1 | 11/2002 | Mason et al. | |
| 6,589,229 B1 * | 7/2003 | Connelly | A61M 5/14248 604/65 |
| 6,656,159 B2 | 12/2003 | Flaherty | |
| 6,723,072 B2 | 4/2004 | Flaherty et al. | |
| 6,740,059 B2 | 5/2004 | Flaherty | |
| 7,686,787 B2 | 3/2010 | Moberg et al. | |
| 7,794,434 B2 * | 9/2010 | Mounce | A61J 1/1406 604/131 |
| 8,277,415 B2 | 10/2012 | Mounce et al. | |
| 8,696,570 B2 | 4/2014 | Yodfat et al. | |
| 9,138,534 B2 * | 9/2015 | Yodfat | A61M 5/14248 |
| 2002/0169439 A1 | 11/2002 | Flaherty | |
| 2005/0107743 A1 * | 5/2005 | Fangrow, Jr. | A61M 5/158 604/164.01 |
| 2005/0251097 A1 | 11/2005 | Mernoe | |
| 2006/0122577 A1 | 6/2006 | Poulsen et al. | |
| 2006/0264835 A1 | 11/2006 | Nielsen et al. | |
| 2007/0106218 A1 | 5/2007 | Yodfat et al. | |
| 2008/0051709 A1 | 2/2008 | Mounce et al. | |
| 2008/0097327 A1 * | 4/2008 | Bente | A61J 1/1406 604/155 |
| 2008/0097375 A1 * | 4/2008 | Bikovsky | A61M 5/1413 604/500 |
| 2008/0215035 A1 * | 9/2008 | Yodfat | A61M 5/14248 604/513 |

FOREIGN PATENT DOCUMENTS

| | | |
|---|---|---|
| WO | 02068015 A2 | 9/2002 |
| WO | 2005065748 A1 | 7/2005 |
| WO | 2005072794 A2 | 8/2005 |
| WO | 2006108809 A1 | 10/2006 |
| WO | 2008012817 A1 | 1/2008 |
| WO | 2008122983 A1 | 10/2008 |
| WO | 2008139459 A1 | 11/2008 |
| WO | 2008139460 A2 | 11/2008 |
| WO | 2009125398 A2 | 10/2009 |

OTHER PUBLICATIONS

Written Opinion of the International Searching Authority for PCT/IL2008/000641, dated Jan. 19, 2009.

Extended European Search Report, completed Sep. 4, 2018, pertaining to Application No. EP18171458.5.

\* cited by examiner

POSITIVE DISPLACEMENT PUMP

CROSS-REFERENCE TO RELATED APPLICATIONS

This application is filed as a continuation of U.S. application Ser. No. 12/451,435 filed on Nov. 12, 2009, which is a national stage entry of PCT/IL2008/000641 filed May 11, 2008 which claims priority to U.S. Provisional Application Ser. Nos. 60/928,815, 60/928,751 and 60/928,750, all of which were filed in the U.S. Patent & Trademark Office on May 11, 2007. The present application incorporates herein by reference the disclosure of each of the above-referenced applications in its entirety.

The present application relates to U.S. patent application Ser. No. 12/451,430, entitled "Methods And Apparatus For Monitoring Rotation Of An Infusion Pump Driving Mechanism", which claims priority to U.S. Provisional Patent Application No. 60/928,751, filed May 11, 2007, and U.S. patent application Ser. No. 12/451,427, entitled Fluid Delivery Device, which claims priority to U.S. Provisional Patent Application No. 60/928,750, entitled "Fluid Delivery Device", and filed on May 11, 2007. This application incorporates the disclosures of each of these applications herein by reference in their entireties.

FIELD OF THE INVENTION

The present invention generally relates to devices and methods for sustained medical infusion of fluids. Particularly, the present invention relates to a miniature portable infusion device that can be connected and disconnected to and from the body of a patient and that can accurately dispense fluids. Further, the present invention relates to an infusion pump that has two parts: a disposable part and a reusable part. The disposable part contains a thin reservoir.

BACKGROUND OF THE INVENTION

Medical treatment of several illnesses requires continuous drug infusion into various body compartments, such as subcutaneous and intra-venous injections. Diabetes mellitus patients, for example, require administration of varying amounts of insulin throughout the day to control their blood glucose levels. In recent years, ambulatory portable insulin infusion pumps have emerged as a superior alternative to multiple daily syringe injections of insulin. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to individual prescription, since an overdose or under-dose of insulin could be fatal.

Several ambulatory insulin infusion devices are currently available on the market. Mostly, these devices have two portions: a reusable portion that contains a dispenser, a controller and electronics, and a disposable portion that contains a syringe-type reservoir, a needle assembly with a cannula and a penetrating member, and fluid delivery tube. Usually, the patient fills the reservoir with insulin, attaches the needle and the delivery tube to the exit port of the reservoir, and then inserts the reservoir into the pump housing. After purging air out of the reservoir, tube and needle, the patient inserts the needle assembly, penetrating member and cannula, at a selected location on the body, and withdraws the penetrating member. To avoid irritation and infection, the subcutaneous cannula must be replaced and discarded after 2-3 days, together with the empty reservoir. Examples of first generation disposable syringe-type reservoir and tubes were disclosed in U.S. Pat. No. 3,631,847 to Hobbs, U.S. Pat. No. 3,771,694 to Kaminski, U.S. Pat. No. 4,657,486 to Stempfle, and U.S. Pat. No. 4,544,369 to Skakoon. The driving mechanism of these devices is a screw thread driven plunger controlling the programmed movement of a syringe piston.

Other dispensing mechanisms have been also discussed, including peristaltic positive displacement pumps, in U.S. Pat. No. 4,498,843 to Schneider and U.S. Pat. No. 4,715,786 to Wolff. These devices represent an improvement over multiple daily injections, but nevertheless, they all suffer from several drawbacks. The main drawback is the large size and the weight of the device, caused by the configuration and the relatively large size of the driving mechanism of the syringe and the piston. This relatively bulky device has to be carried in a patient's pocket or attached to the belt. Consequently, the fluid delivery tube is long, usually longer than 60 cm, in order to permit needle insertion at remote sites of the body. These uncomfortable bulky devices with a long tube are rejected by the majority of diabetic insulin users, since they disturb regular activities, such as sleeping and swimming. Furthermore, the effect of the image projected on the teenagers' body is unacceptable. In addition, the delivery tube excludes some optional remote insertion sites, like buttocks, arms and legs.

To avoid the consequences of long delivery tube, a new concept, of second generation pump, was proposed. This concept includes a remote controlled skin adherable device with a housing having a bottom surface adapted to contact patient's skin, a reservoir disposed within the housing, and an injection needle adapted to communicate with the reservoir. These skin adherable devices should be disposed every 2-3 days similarly to available pump infusion sets. These devices were disclosed at least in U.S. Pat. No. 5,957,895 to Sage, U.S. Pat. No. 6,589,229 to Connelly, and U.S. Pat. No. 6,740,059 to Flaherty. Additional configurations of skin adherable pumps were disclosed in U.S. Pat. No. 6,723,072 to Flaherty and U.S. Pat. No. 6,485,461 to Mason. These devices also have several limitations: they are bulky and expensive, their high selling price is due to the high production and accessory costs, and the user must discard the entire device every 2-3 days, including relatively expensive components, such as driving mechanism and other electronics.

There are various types of conventional pumping mechanisms that are employed in infusion devices. An example of a pumping mechanism is a syringe type in which a motor driven plunger displaces the fluid out of a round barrel-shaped reservoir. A processor-controlled motor allows pre programming and on demand fluid dispensing.

Such syringe type mechanism is discussed for example in the following US patents referring to the first pump generation: U.S. Pat. No. 3,858,581 to Kamen, U.S. Pat. No. 4,435,173 to Siposs, U.S. Pat. No. 4,652,260 to Fenton, U.S. Pat. No. 5,954,697 to Strisathapat. Syringe reservoir is also described in U.S. patents and applications referring to the second pump generation: U.S. Pat. No. 6,656,159 to Flaherty and U.S. Patent Application No. 2005/0251097 to O'Neill.

Unfortunately the second generation skin adherable infusion devices suffer from major drawbacks which include, inter alia, the following:

They are heavy and bulky—syringe-type reservoirs are usually rounded tubes, thus, to hold, for example, 3 ml of drug, they should either be long and having a small diameter (e.g., 60 mm long×8 mm inner diameter) or short and having a large diameter (e.g., 17 mm long×15 mm inner diameter). This is a major hurdle for all portable insulin infusion devices used for treatment of diabetes patients and, especially, for second generation skin adherable insulin pumps.

They are expensive to manufacture and replace—the entire device including relatively expensive components (electronics, driving mechanism, etc.) should be disposed every 3 days.

Reservoir filling may require an additional syringe to draw the fluid from the glass bottle and to subsequently fill the pump reservoir.

They cannot be disconnected—there are situations in which patients would like to disconnect the pump (e.g., during hot showers, sauna, intimacy, etc.), however, conventional pumps do not allow such disconnection.

The cannula is rigidly secured at the pump housing, thus, users cannot choose cannula length and vary the insertion angle.

Waste of insulin—in cases of site misplacement (e.g., scarred tissue, bleeding, cannula kinking, etc.) the entire device including the filled insulin reservoir should be disposed, which wastes costly insulin.

SUMMARY OF THE INVENTION

The present invention overcomes the deficiencies of the above conventional devices by providing, in some embodiments, a miniature portable programmable fluid dispensing device (hereafter a "dispensing patch" or "dispensing unit", whereby the terms "unit" and "patch" are used interchangeably in the following description) that does not have long external tubing and can be attached (and detached) to the patient at any desired location on the body. In some embodiments, the present invention is a simple and inexpensive dispensing patch that has two parts: a disposable part and a reusable part. After connection of the reusable part and the disposable part, the whole device has a thin profile and a relatively small footprint on the body of the patient (i.e., discreet). In some embodiments, the present invention relates to a dispensing patch that can be connected to (or reconnected to) and disconnected from the body of the patient in a safe, reliable, and user-friendly manner. Connections (or reconnections or disconnections) neither affect the components of the dispensing patch nor harm the surrounding body tissues.

In some embodiments, the present invention relates to a dispensing patch that delivers fluid to the body of the patient via a soft cannula, wherein insertion of the cannula can be done either manually or automatically using a dedicated inserter. In some embodiments, the fluid can be delivered using a soft cannula and the cannula can be inserted at any desired angle. Further, the length of the cannula can be tailored to the needs of the patient.

In some embodiments, the present invention relates to a dispensing patch for delivering fluid to the body of the patient, wherein the patch has two parts: a disposable part having few parts that are easy to manufacture and assemble as well as cheap and a reusable part. In some embodiments, the disposable part includes a syringe-type reservoir, which is configured as a flat container maintaining thin profile. In some embodiments, the syringe-type reservoir can draw fluid from a glass bottle. Further, the sealing between the disposable and reusable parts subsequent to their connection does not affect the functionalities of the device.

In some embodiments, the present invention relates to a device that can deliver therapeutic fluid into the body. The fluid delivery device of the invention comprises 3 units: a dispensing unit, a skin adherable needle unit, and a remote control unit. The dispensing unit can be connected to and disconnected from the skin adherable needle unit, and the remote control unit communicates with the dispensing unit allowing programming, user inputs and data acquisition.

In some embodiments, the dispensing unit includes a driving mechanism and a pumping mechanism, a reservoir and an outlet port. The outlet port allows connection of the dispensing unit to and disconnection from the needle unit. The outlet port is provided with a connecting element (e.g., a connecting lumen) that can pierce a self-sealable rubber septum that seals the outlet port. The connecting lumen allows fluid communication between the dispensing unit and the needle unit. The dispensing unit can be configured as a single part. In some embodiments, the dispensing unit includes at least one reservoir, tubes, batteries, driving and pumping mechanisms, electronics and other auxiliary components, e.g., an occlusion sensor.

In some embodiments, the dispensing unit can be also configured as a two-part unit having a reusable part and a disposable part, where
 a. The reusable part contains a driving mechanism and a pumping mechanism, electronics and other relatively expensive components e.g., an occlusion sensor.
 b. The disposable part contains inexpensive components such as at least one reservoir, tubes and batteries that can supply energy until reservoir emptying, usually for a few days.

In some embodiments, the needle unit includes the following:
 a. A cannula and a penetrating member. The penetrating member is to be removed after insertion.
 b. A cradle—a flat sheet with adhesive layer facing the skin and carrying a connecting means on its upper side allowing connection to and disconnection from the dispensing unit. Upon insertion of the cannula the cradle remains adhered to the skin by virtue of adhesive layer. The cradle anchors the cannula and allows connection to the dispensing unit. The cradle can be rigidly connected to the cannula and to the well or it can be a stand-alone separate item.
 c. A well—a tubular protrusion emerging upwardly from the cradle to allow alignment with the outlet port of the dispensing unit and appropriate connection between the needle and the dispensing units as required for proper fluid delivery to the body.

In some embodiments, the remote control unit includes means for programming fluid flow, controlling the dispensing unit, and data acquisition and indications (e.g., display).

In some embodiments, the present invention's dispensing unit can also be provided with appropriate input means, e.g., buttons enabling issuing of flow instructions.

In some embodiments, the dispensing unit includes two parts, reusable and disposable. The disposable part contains reservoir, batteries and outlet port, and the reusable part contains electronics, driving and pumping mechanism. The reservoir has a substantially flat profile cross-section. Such cross-section can be for example oval, elliptical or rectangular. By virtue of this provision, the entire disposable part is very thin (for example, less than 15 mm). The reservoir is a part of a syringe fitted with a displaceable piston plunger. The outlet port of the reservoir is connected by a tubular connection, e.g., connecting lumen to the outlet port of the dispensing unit. The outlet port of the dispensing unit is configured and dimensioned to precisely fit to a standard drug glass bottle cork. Reservoir filling is carried out by engagement of the outlet port with the bottle's rubber cork. The connecting lumen pierces the rubber cork enabling drug drawing from the bottle upon backward plunger movement while the bottle is positioned upside down.

Upon connection of the filled disposable part and reusable part, the electronics in the reusable part receive power supply from the batteries (as can be understood by one skilled in the art, there can be a single battery) provided in the disposable part. The driving mechanism is enabled and can push the piston plunger based on preprogrammed and/or on-demand fluid delivery commands. Disconnection and reconnection of the dispensing unit from and to the needle unit can be carried out upon patient discretion.

Thus, it is an object of some of the embodiments of the present invention to provide a method, a system and a device for medical infusion of fluids into the body.

It is an object of some of the embodiments of the present invention to provide a device for sustained medical infusion with controlled rate injection of a fluid into a body.

It is an object of some of the embodiments of the invention to provide a device for medical infusion that contains a dispensing unit that is thin, has no external tubing and can be attached to any location of the body.

It is an object of some of the embodiments of the invention to provide a device for medical infusion that contains a dispensing unit that comprises at least one reservoir, and an outlet port, which can be brought in direct fluid communication with a skin adherable needle unit.

It is an object of some of the embodiments of the invention to provide a device for medical infusion that contains a skin adherable needle unit. The skin adherable unit includes a subcutaneous cannula and a well that allows fluid communication between the dispensing unit and the subcutaneous compartment in the patient's body.

It is an object of some of the embodiments of the invention to provide a dispensing unit that can be configured as a single part unit, or as a two-part unit having a reusable part and disposable part. The reusable part contains electronics, driving mechanism and pumping mechanism and other relatively expensive components e.g., a sensor for detection of occlusion, and the disposable part contains reservoir, and outlet port. Batteries can reside in the disposable part and/or in the reusable part.

It is an object of some of the embodiments of the invention to provide a device employing a dispensing unit that can be disconnected and reconnected.

It is an object of some of the embodiments of the present invention to provide an infusion device that contains three units—a remote control unit, a dispensing unit and a needle unit. Wherein the dispensing unit or so-called patch can be connected/disconnected to/from the needle unit and wherein the needle unit is adherable to the skin. Infusion programming can be carried out by the remote control unit or by at least one control button located on the patch.

It is an object of some of the embodiments of the present invention to provide an infusion device that contains a dispensing unit that can be connected to and disconnected from a needle unit. The needle unit includes a skin compliant cradle that is fitted with a cannula and a well.

It is an object of some of the embodiments of the present invention to provide an infusion device that contains a dispensing unit that can be connected to and disconnected from a skin compliant cradle. A needle unit that contains cannula and well can be inserted through the cradle into the skin.

It is an object of some of the embodiments of the invention to provide an infusion device that contains a dispensing unit that is composed of at least one part and another unit (needle unit) has a cradle, a well, and a cannula. The cradle has an adhesive layer on its bottom side allowing adherence to the skin, and attachment means is provided on its upper side allowing connection of the dispensing unit to the cradle. The well is connected at its lower side to the cannula and has a rubber septum (i.e., silicone, chlorobutyl) at its upper side.

The outlet port of the dispensing unit is provided with a short connecting element having a sharp hollow tip for fluid communication between the dispensing unit and the well. This connecting element, which will be referred to also as a "connecting lumen" allows multiple piercing of the rubber septum and fluid communication between the reservoir and cannula.

It is an object of some of the embodiments of the present invention to provide a method that allows infusion of a fluid into the patient's body through a flexible soft transdermal cannula. The cannula can be inserted in the patient's body either manually or by a dedicated spring loaded inserter.

It is an object of some of the embodiments of the present invention to provide a method that allows the adherence of a cradle to a patient skin surface by an adhesive means, thus providing fixation of the cannula and an anchoring base for the dispensing unit.

It is another object of some of the embodiments of the invention to provide a method enabling the connection of the dispensing unit to and disconnection from the needle unit, connecting the outlet port of the dispensing unit to the well, connecting the dispensing patch housing to the cradle and piercing the rubber septum by the connecting lumen.

It is another object of some of the embodiments of the invention to provide a safe, simple, reliable and user-friendly method for connecting and disconnecting a dispensing unit to the patient while maintaining sterility and avoiding damage to the patient and/or infusion device.

BRIEF DESCRIPTION OF DRAWINGS

A detailed description of embodiments of the invention will be made with reference to the accompanying drawings, wherein like reference numerals designate corresponding parts in the several figures.

DETAILED DESCRIPTION OF THE INVENTION

To overcome limitations of the conventional systems, as well as, to avoid price limitations and to extend patient customization, a third generation of skin-adherable dispensing patches was proposed. An example of such device is described in co-pending/co-owned U.S. patent application Ser. No. 11/397,115 and International Patent Application No. PCT/IL06/001276, disclosures of which are incorporated herein by reference in their entireties. In this device, a dispensing unit included two parts:

A reusable part containing the driving and pumping mechanism, electronics and other relatively expensive components; and A disposable part containing inexpensive components such as reservoir, tubes and batteries.

This concept provides a cost-effective solution and allows diverse usage of the device, e.g., the use of various reservoir sizes. An improvement to a skin-adherable pump having two parts is described in co-pending/co-owned U.S. Provisional Patent Application Ser. No. 60/876,679, U.S. patent application Ser. No. 12/004,837, and International Patent Application No. PCT/IL07/001578, the disclosures of which are incorporated herein by reference in their entireties. In these applications, a method for connection and disconnection of a skin adherable pump is disclosed. The method uses a cradle, which is initially adhered to the skin and then a cannula is inserted through the cradle into the body. The two-part pump can be consequently connected and disconnected to and from the cradle upon patient discretion.

This concept allows versatile operational modes including manual and automatic cannula insertion, allows use of cannulae with various lengths and allows their insertion at various insertion angles.

The present invention overcomes all deficiencies of the conventional systems and is discussed with regard to FIGS. 1-30b below.

Figure 1:
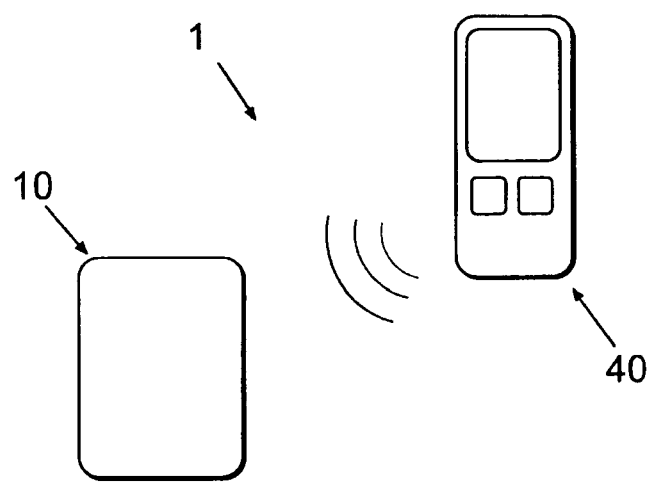
FIG. 1 illustrates an exemplary fluid dispensing device including the dispensing unit and the remote control unit, according to some embodiments of the present invention.

FIGS. 1-5b show an exemplary fluid dispensing device (1) and various options for attaching it to the body of a patient, according to some embodiments of the present invention. FIG. 1 shows the device (1) for medical infusion of therapeutic fluids into the body of the patient. The device (1) includes a dispensing unit (10) and a remote control unit (40). The dispensing unit (10) communicates with the remote control unit (40) that can forward commands, receive and process instructions from the dispensing unit (10), etc. The remote control unit (40) can include a display and a plurality of buttons to control operation of the units (10) and (40). The units (10) and (40) can communicate with a wireless, wired, wire line, RF or any other type communication. The unit (40) can be a personal computer, a laptop, an iPod, a PDA, a cellular telephone, a remote control, or any other suitable device.

Figure 2A:
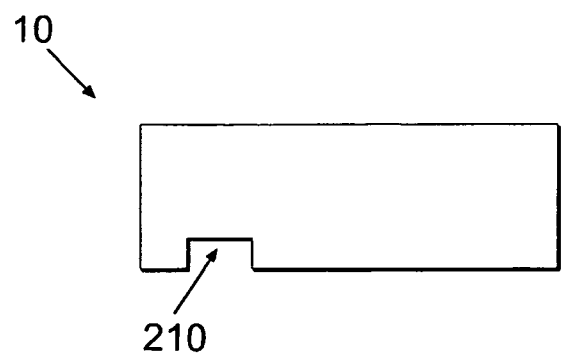
FIGS. 2a-b illustrate exemplary single part and two-part dispensing units, according to some embodiments of the present invention.
Figure 2B:
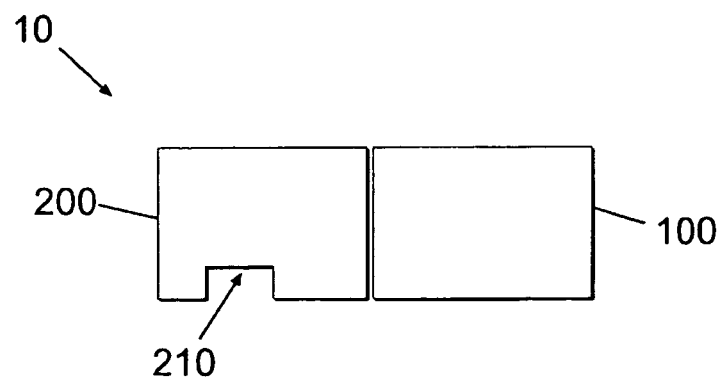

FIGS. 2a-b show additional details of the dispensing unit (10). The dispensing unit can have a single part (as shown in FIG. 2a) or two parts (as shown in FIG. 2b). The two-part dispensing unit (10) includes a reusable part (100) and a disposable part (200), where the disposable part (200) includes an outlet port (210). The single-part unit (10) can also include an outlet port (210). In some embodiments, the dispensing unit (10) includes the outlet port (210) on its lower surface. The outlet port (210) is in fluid communication with a reservoir (not shown) disposed in the unit (10) and allows fluid dripping during priming and delivery of therapeutic fluid to the body of the patient.

Figure 3A:
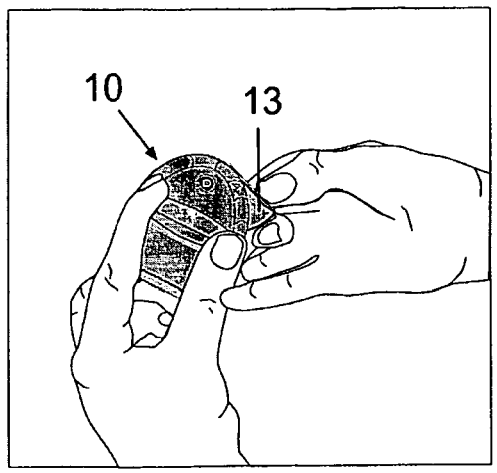
FIGS. 3a-c illustrate an exemplary direct attachment of dispensing unit to the body, according to some embodiments of the present invention.
Figure 3B:
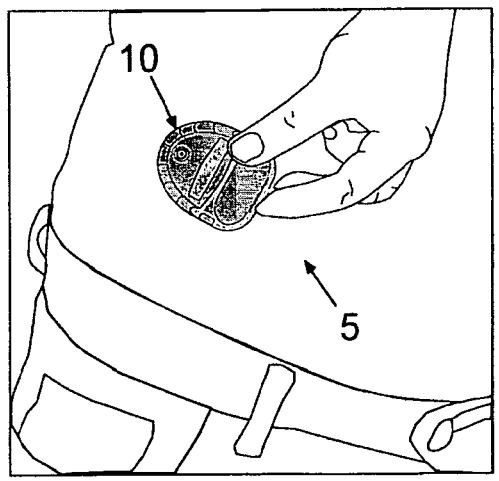
Figure 3C:
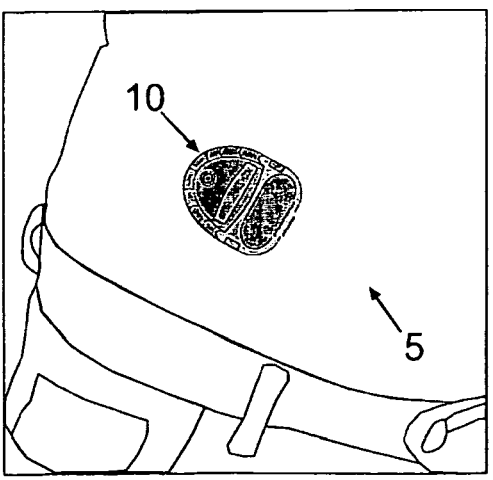

FIGS. 3a-c show an exemplary adherence of the dispensing unit (10) to the skin (5) of the patient, according to some embodiments of the present invention. FIG. 3a shows removal of the adhesive protection layer (13). The adhesive protection layer (13) can be disposed on the bottom portion of the unit (10) and once the layer (13) is removed, the unit (10) can be adhered directly to the patient's skin (5). FIG. 3b shows adhering the dispensing unit (10) to the skin (5). FIG. 3c shows dispensing unit (10) being adhered to the skin (5). As can be understood by one skilled in the art, the unit (10) can be adhered directly to the skin (5) or via an intermediary layer/device.

Figure 4A:
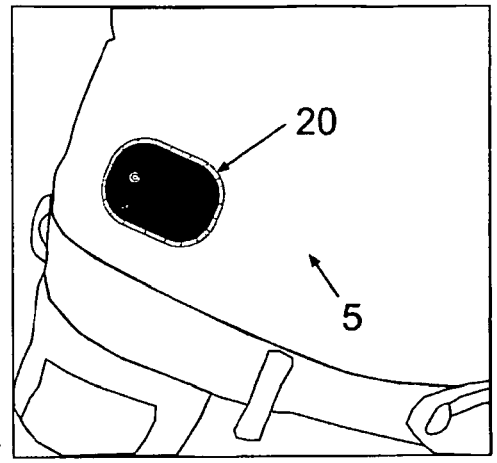
FIGS. 4a-c illustrate an exemplary adherence of the dispensing unit to the patient's skin using a needle unit, according to some embodiments of the present invention.
Figure 4B:
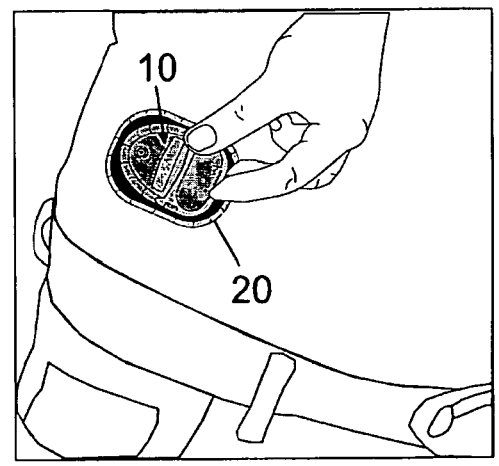
Figure 4C:
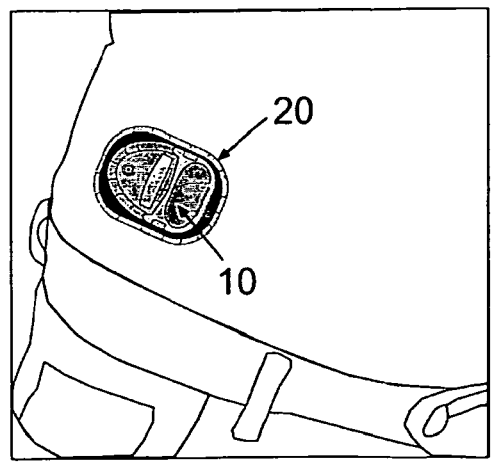

In some embodiments, as shown in FIG. 4a-c, a needle unit (20) can be initially adhered to the skin (5). Then, the dispensing unit (10) can be connected to (and later disconnected from) the needle unit (20) upon patient's discretion. FIG. 4a shows the needle unit (20) adhered to the body of the patient. FIG. 4b shows connection of the dispensing unit (10) to the needle unit (20). FIG. 4c shows the dispensing unit (10) after it has been connected to the needle unit (20) and being ready for operation.

Figure 5A:
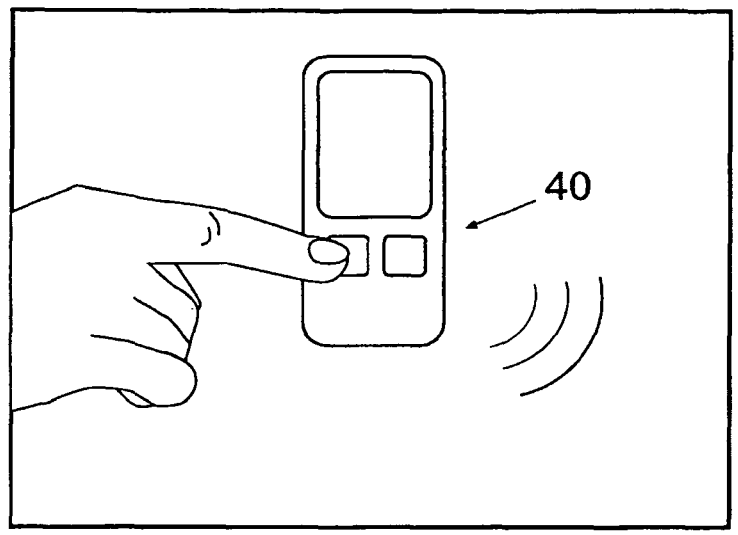
FIGS. 5a-b illustrate exemplary operation modes of the dispensing unit, according to some embodiments of the present invention.
Figure 5B:
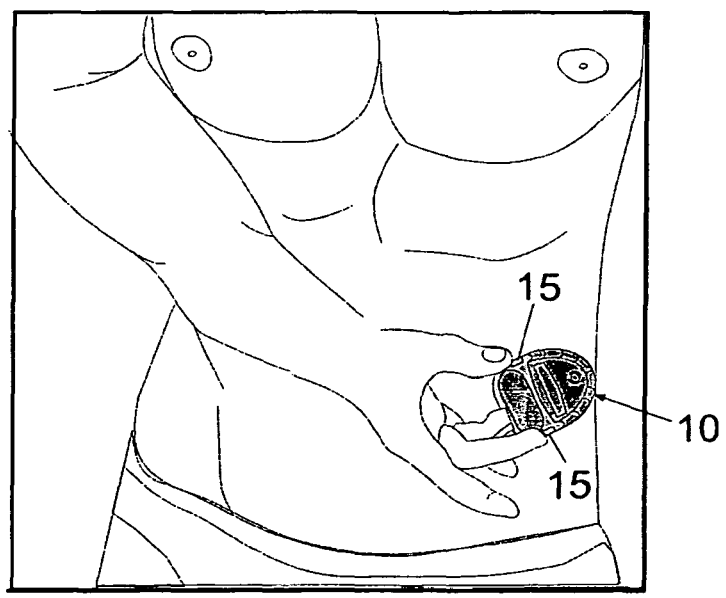

FIGS. 5a-b show various operation modes of the dispensing unit (10), according to some embodiments of the present invention. The patient can operate the dispensing unit (10) either by using the remote control unit (40) (as shown in FIG. 5a) or by using one or more buttons (15) located on the dispensing unit (10), as shown in FIG. 5b. Upon entry of commands, either via the remote control unit (40) or the buttons (15), the unit (10) can perform various functions, such as, dispensing of fluid to the body of the patient, generate feedback on the amount of fluid delivered, generate various alerts, etc.

Figure 6A:
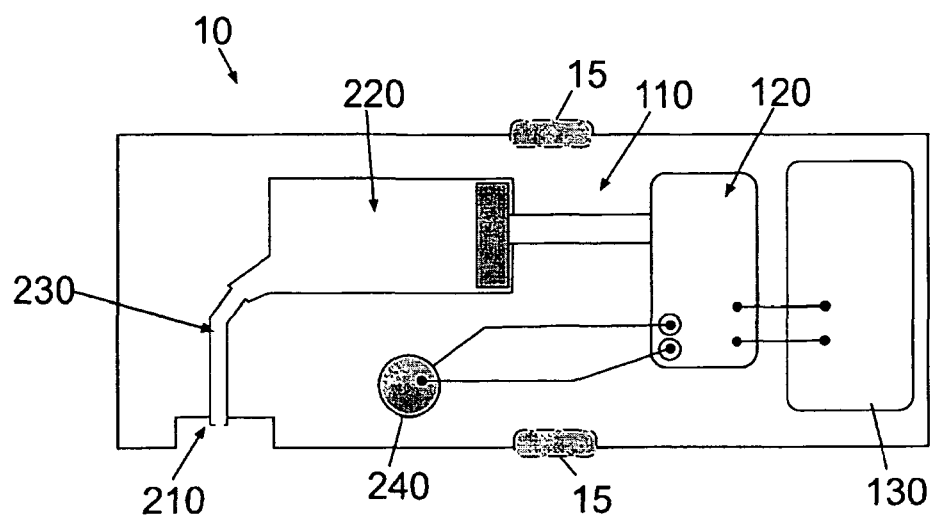
FIGS. 6a-b illustrate exemplary single part and two-part dispensing units including their internal components, according to some embodiments of the present invention.
Figure 6B:
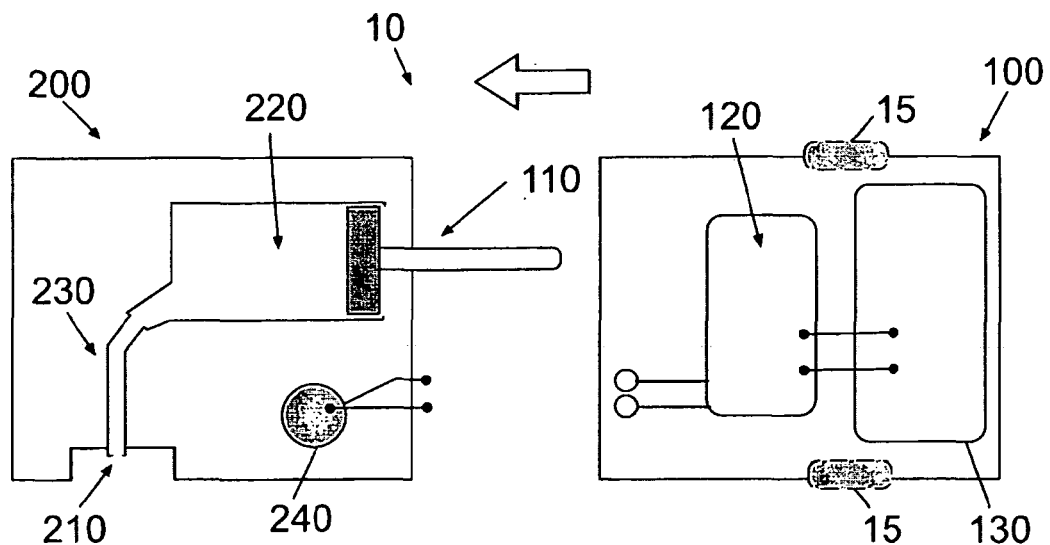

FIGS. 6a-b show an exemplary skin adherable dispensing unit or a "patch unit" (10) employing a syringe pump for dispensing fluid to the body of the patient. FIG. 6a shows a single-part dispensing unit (10). The unit (10) includes a housing that contains a reservoir (220), a fluid delivery tube (230), an outlet port (210), an energy supply (e.g., one or more batteries) (240), an electronics component (130), a driving mechanism (120), and manual buttons (15). The reservoir (220) is in fluid communication with the outlet port (210) via the delivery tube (230) and allows delivery of therapeutic fluid (e.g., insulin) to the body of the patient via the outlet port (210). To pump the fluid from the reservoir (220) into the fluid delivery tube (230); a plunger (110) is fitted within the reservoir (220) and can push the fluid toward the fluid delivery tube (230). The plunger (110) is coupled to the driving mechanism (120) that drives the movement of the plunger (110) inside the reservoir (220). The driving mechanism (120) includes a motor (e.g., a stepper motor, a DC motor, a SMA actuator or the like) and a driving gear for driving the plunger (110). The driving mechanism is controlled by electronics (130), which can include a controller, a processor, a transceiver and other electronic components. The energy supply (240) provides power to the electronics (130) and the driving mechanism (120) for receiving/transmitting commands and for driving the plunger (110) in the reservoir (220). The unit (10) can be programmed using the remote controller (40) (not shown) and/or using one or more buttons (15) provided on the dispensing unit (10). The buttons (15) can turn on/off the unit (10), provide infusion/dispensing instructions, cause transmission/receipt of commands, etc.

FIG. 6b shows an exemplary two-part dispensing unit (10) having a reusable part (100) and a disposable part (200), according to some embodiments of the present invention. The unit (10) uses a pumping mechanism such as a positive displacement pump. The unit (10) shown in FIG. 6b includes similar components as the unit (10) shown in FIG. 6a. However, some of the components are located in the reusable part (100) and other components are located in the disposable part (200).

The reusable part (100) includes the driving mechanism (120) (e.g., motor, gear(s), etc.), electronics (130), at least one button (15), and various electrical connectors. The disposable part (200) includes the reservoir (220) provided with the plunger (110), the energy supply means (240), the fluid delivery tube (230), and the outlet port (210). In some embodiments, the plunger (110) may be located in the reusable part (100) or be shared by the reusable and disposable parts. Infusion programming can be carried out using the remote controller (40) (not shown) and/or using one or more buttons (15) provided on the reusable part (100). Fluid dispensing is possible upon connection (as indicated by an arrow) of the reusable part (100) to the disposable part (200). An embodiment of such two-part unit is disclosed in a co-pending/co-owned U.S. patent application Ser. No. 11/397,115 and International Patent Application No. PCT/IL06/001276, disclosures of which are incorporated herein by reference in their entireties. The operation of the two-part unit (10) shown in FIG. 6b is similar to the operation of the unit (10) shown in FIG. 6a.

FIGS. 7a-13c illustrated exemplary ways of establishing fluid communication between the fluid reservoir (220) and the body of the patient using the dispensing unit (10), according to some embodiments of the present invention.

Figure 7A:
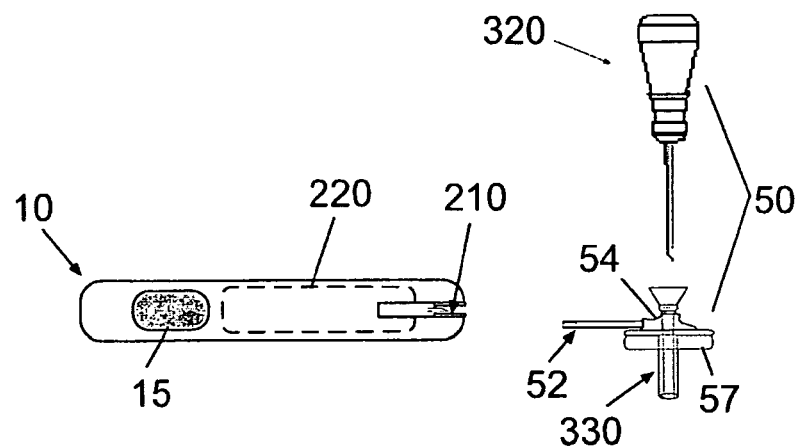
FIGS. 7a-c illustrate an exemplary fluid communication between the dispensing unit and a cannula using an infusion set, according to some embodiments of the present invention.
Figure 7B:
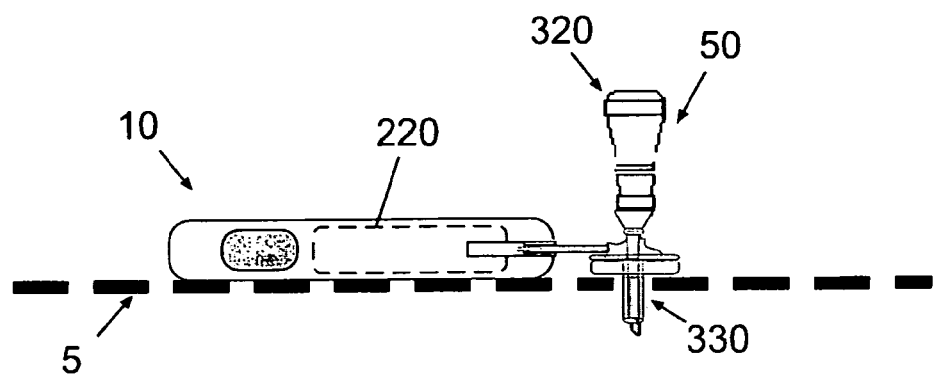
Figure 7C:
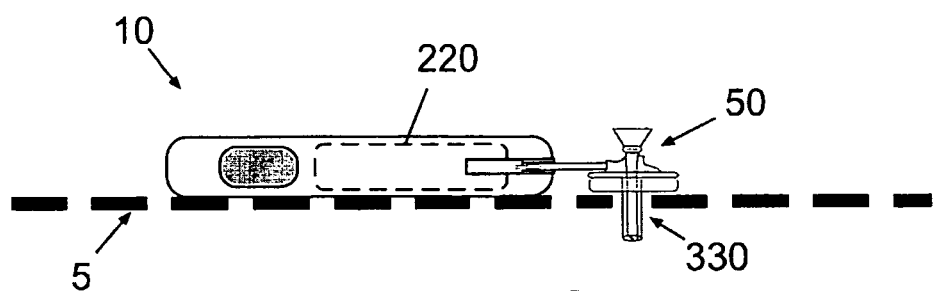

FIGS. 7a-c show an exemplary infusion set (50) for delivering therapeutic fluid (e.g., insulin) to the body of the patient, according to some embodiments of the present invention. As illustrated in FIGS. 7a-c, the infusion set (50) is located outside the housing of the dispensing unit (10). The infusion set (50) includes a connecting tube (52), a hub (54), a cannula (330) and a penetrating member (320). The connecting tube (52) is coupled to the hub (54) and is in fluid communication with the cannula (330). The hub (54) accommodates insertion of the penetrating member (320) into the cannula (330). Upon insertion of the penetrating member (320) through the cannula (330), the penetrating member (320) can pierce the skin (5) (not shown in FIG. 7a) of the patient and allow insertion of the cannula (330) into a subcutaneous compartment (i.e., located under the skin of the patient). The hub (54) can also include an adhesive layer (57) that can be adhered to the skin (5) in order to secure hub (54) to the skin during fluid delivery. To allow fluid delivery via the infusion set (50), the connecting tube (52) is connected to (or inserted into) the outlet port (210). The outlet port (210) may be provided with a connector e.g., Luer lock connector, for establishing a reliable and/or sealed connection between the infusion set (50) and dispensing unit (10).

Upon insertion of the connecting tube (52) into the outlet port (210), the reservoir (220) and the cannula (330) are in fluid communication with each other and therapeutic fluid can be delivered from the reservoir (220) into the body of the patient via the cannula (330).

FIG. 7b shows the dispensing unit (10) directly adhered to the skin (5) and connected to the infusion set (50), as discussed above. As illustrated, the penetrating member (320) has been inserted into the hub (54) and the cannula (330) and has pierced the skin (5) of the patient allowing the cannula (330) and the penetrating member (320) to protrude into the subcutaneous compartment. The penetrating member (320) may include a piercing portion (e.g., a dagger, etc.) that can pierce the skin of the patient and thereby allow insertion of the cannula (330). While the penetrating member (320) is disposed inside the hub (54) and the cannula (330), the fluid is not being delivered to the patient.

FIG. 7c illustrates the unit (10) being connected to the infusion set (50) subsequent to the withdrawal of the penetrating member (320). Once the penetrating member is withdrawn, the fluid communication is established between cannula (330) and reservoir (220) of the dispensing unit (10) and the fluid can be delivered to the patient.

FIGS. 8a-10d illustrate embodiments of the dispensing unit (10) that uses a well (60) along with a penetrating cartridge (62) connecting the reservoir (220) with the cannula (330), according to some embodiments of the present invention. An exemplary embodiment of this system is disclosed in co-pending/co-owned U.S. Provisional Patent Application Ser. Nos. 60/833,110 and 60/837,877, and International Patent Application PCT/IL07/000932, the disclosures of which are incorporated herein by reference in their entireties.

Figure 8A:
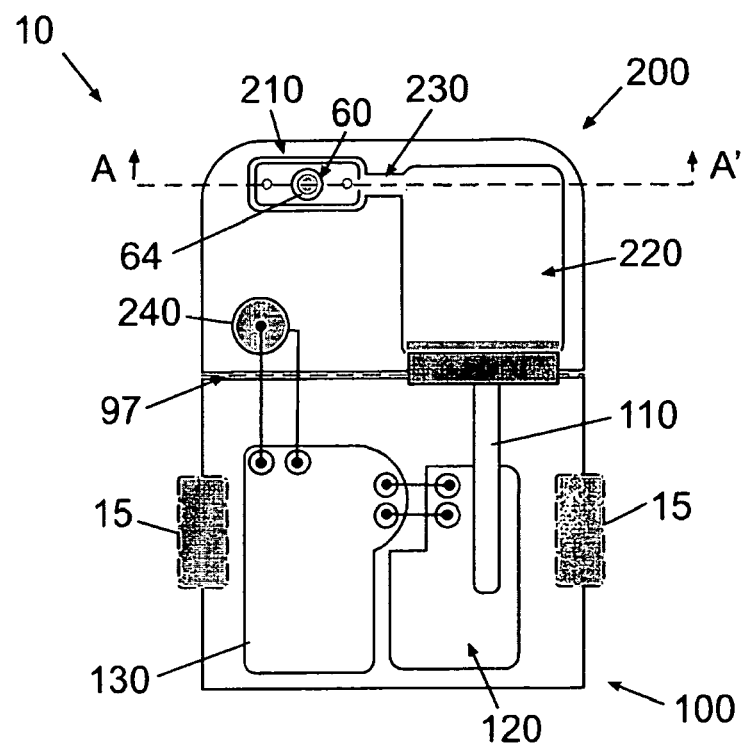
FIGS. 8a-b illustrate an exemplary dispensing unit having a well, according to some embodiments of the present invention.

FIG. 8a shows an exemplary two-part dispensing unit (10). As above, the dispensing unit (10) includes the reusable part (100) and the disposable part (200) for connecting with the reusable part (100). The reusable part (100) includes the plunger (110), the driving mechanism (120) (e.g., the motor, gear, and other components), the electronics (130), buttons (15), and connecting leads coupling various electronics (130) components and the battery (240). The disposable part (200) includes the battery (240), the reservoir (220), the fluid delivery tube (230), and the outlet port (210). As above, the reservoir (220) is in fluid communication with the outlet port (210) via the fluid delivery tube (230). The outlet port (210) further includes the well (60) that is in fluid communication with the reservoir (220) via the fluid delivery tube/tubular connector (230). The well (60) is provided with an opening (64) through which the penetrating cartridge (320) and the cannula (330) can be inserted (not shown in FIG. 8a).

The reusable part (100) and the disposable part (200) can be coupled to each using latches, a snap-fit arrangement, or any other suitable arrangement. In some embodiments, a hermetic seal (97) can be placed between parts (100) and (200) to prevent entry of contaminants or other outside elements. As further shown in FIG. 8a, the plunger portion (that pushes the fluid toward the outlet port (210)) of the plunger (110) is contained within the reservoir (220) and a shaft portion of the plunger (110) is disposed partially in the reusable part (100) and the disposable part (200). The shaft portion of the plunger (110) is coupled to the driving mechanism (120), which pushes the shaft portion, and is configured to move between the parts (100) and (200). For example, during reservoir-filling procedures, the shaft portion of the plunger (110) is moved backward away from the reservoir (220); and during dispensing procedures, the shaft portion of the plunger (110) is moved toward the reservoir (220) thereby pushing the fluid into the fluid delivery tube (230) and the outlet port (210).

Figure 8B:
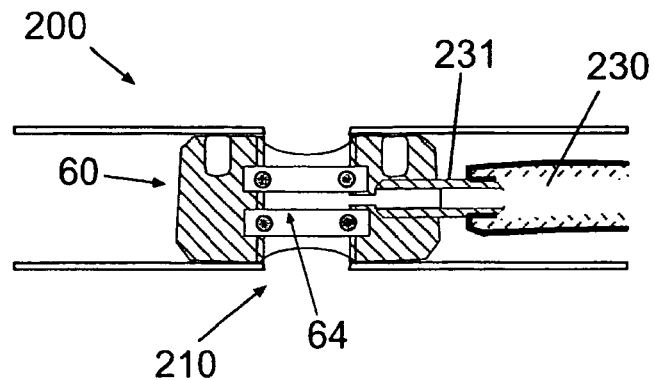

FIG. 8b is a cross-sectional view of the well (60) located in the disposable part (200) taken along direction A-A' of FIG. 8a. As shown in FIG. 8b, the well (60) is in fluid communication with the fluid delivery tube (230). In some embodiments, the fluid delivery tube (230) can be coupled to a connector tube (231). The connector tube (231) is in fluid communication with the opening (64). Once the penetrating member (320) is removed from the opening (64), the fluid can pass from the fluid delivery tube (230) via connector tube (231) and into the opening (64) toward the outlet port (210) for delivery to the patient. The connection between the connector tube (231) and the fluid delivery tube (230) is a sealed connection that prevents slippage of the fluid delivery tube (230) from the connector (231) as well as any leakage of fluid or entry of contaminants into the opening (64). In some embodiments, the opening (64) can also include a septum component that seals the opening (64) upon removal of the penetrating member (320). The septum also prevents entry of contaminants into the well (60) and leakage of fluid.

Figure 9A:
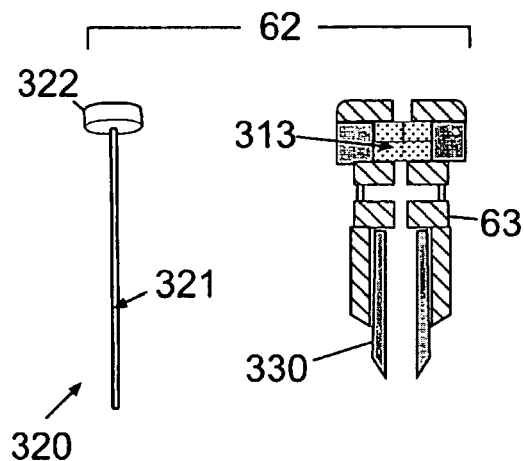
FIGS. 9a-b illustrate exemplary penetrating cartridge and penetrating member for use with the well, according to some embodiments of the present invention.
Figure 9B:
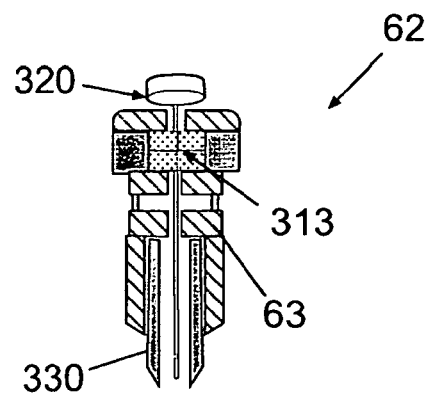

FIG. 9a shows an exemplary penetrating cartridge (62), according to some embodiments of the present invention. The penetrating cartridge (62) includes a body portion (63), the cannula (330), a self-sealable septum (313), and the penetrating member (320). The penetrating member (320) can be configured as a dagger (321) with a sharp tip and with a grip portion (322). The penetrating member (320) is adapted to pierce the surface of the skin (5) (not shown in FIG. 9a). The penetrating member (320) is inserted through the septum (313) and the cannula (330). The septum (313) seals the passageway (which includes cannula (330)) within the body portion (63) of the penetrating cartridge (62). Once the penetrating member (320) is removed from the passageway within the body portion (63), the septum (313) seals the passageway. FIG. 9a illustrates the septum (313) sealing such passageway. FIG. 9b shows the penetrating member (320) being placed inside the penetrating cartridge (62).

FIGS. 10a-d show exemplary insertion and subcutaneous placement of the cannula (330) using a dedicated inserter (70), according to some embodiments of the present invention. An exemplary embodiment of the inserter (70) has been already disclosed in co-pending/co-owned U.S. Provisional Patent Application Ser. No. 60/861,345, disclosure of which is incorporated herein by reference in its entirety.

Figure 10A:
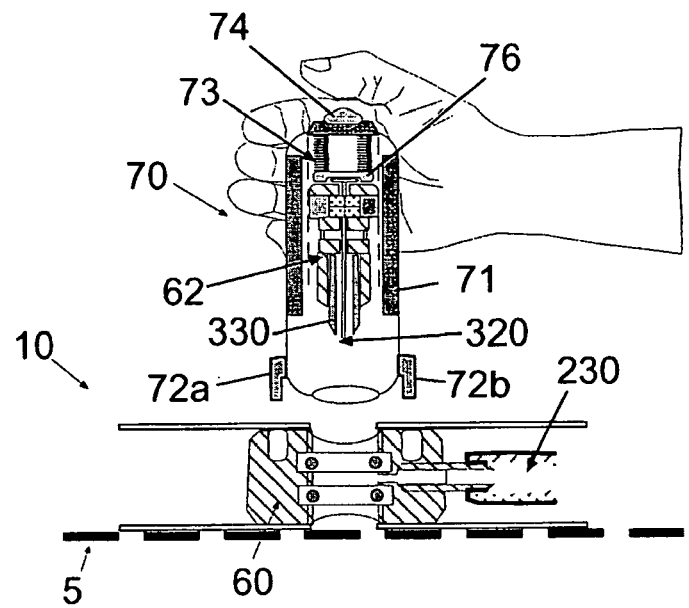
FIGS. 10a-d illustrate an exemplary cannula insertion using the well shown in FIGS. 8a-b, according to some embodiments of the present invention.

FIG. 10a is a cross-sectional view of the well (60) and an inserter (70), where the inserter (70) is loaded with the penetrating cartridge (62). The inserter (70) includes a housing (71), a spring-firing mechanism (73), a release button (74), a penetrating member holding platform (76), and projections (72a) and (72b). The release button (74) is coupled to the spring-firing mechanism (73) and allows release of the spring-firing mechanism (73) for the purposes of inserting the penetrating cartridge (62) into the well (60) (and penetrating the skin (5) with the penetrating member (320). The projections (72a) and (72b) are coupled to the housing (71) and are configured to mate with corresponding recesses (66a) and (66b) of the well (60). The projections (72a) and (72b) and recesses (66a) and (66b) provide requisite stability to the housing (71) during insertion of the penetrating cartridge (62) into the well (60). As illustrated in FIG. 10a, the housing (71) is loaded with the penetrating cartridge (62) (along with the penetrating member (320) and cannula (330)) and the spring-firing mechanism (73) is in a compressed state (e.g., the spring is compressed). The holding platform (76) secures the penetrating cartridge (62) prior to being inserted into the well (60).

Figure 10B:
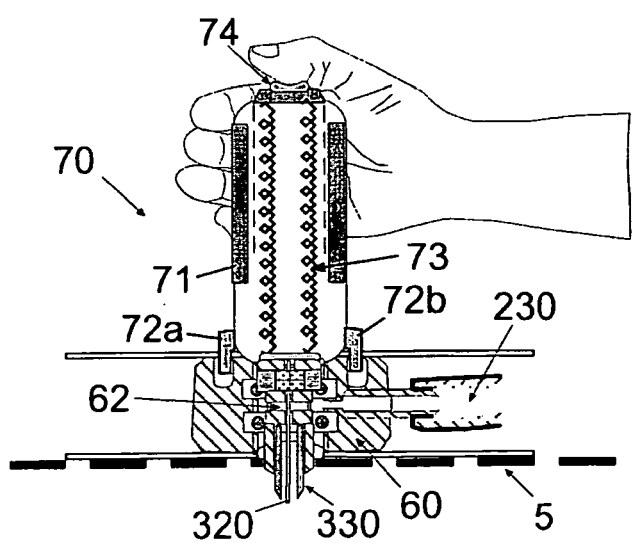
Figure 10C:
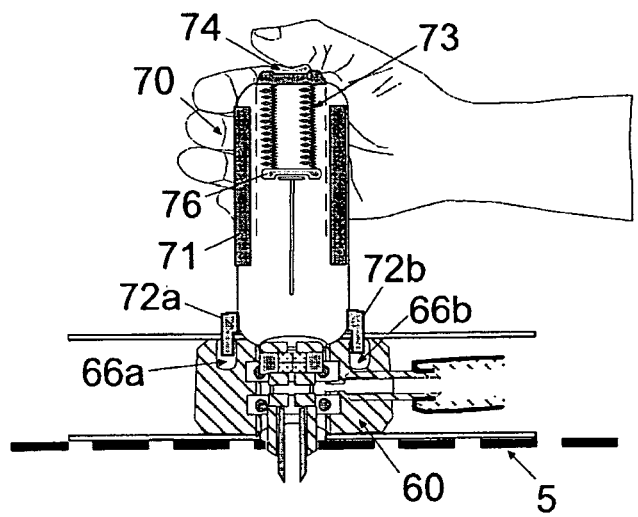

To insert the penetrating cartridge (62) into the well (60), the user/patient aligns the projections (72a) and (72b) with the recesses (66a) and (66b) and secures the housing (71) opposite the well (60). Then, the user/patient depresses the button (74) and the spring-firing mechanism (73) is released. Once the spring-firing mechanism is released, the penetrating cartridge (62) is inserted into the well (60) and the penetrating member (320) punctures the skin of the patient. Along with the puncturing of the skin (5), the cannula (330) loaded into the penetrating cartridge (62) is inserted into the subcutaneous compartment of the patient. Once the skin (5) is punctured, the spring-firing mechanism (73) is compressed and the penetrating member (320) is removed from the penetrating cartridge (62). Once the penetrating member (320) is removed, the penetrating cartridge (62) along with the cannula (330) remains lodged in the well (60). In some embodiments, the penetrating cartridge (62) and the penetrating member (320) are inserted simultaneously or one after another using the spring-firing mechanism. The above procedures are illustrated in FIGS. 10b-c.

Figure 10D:
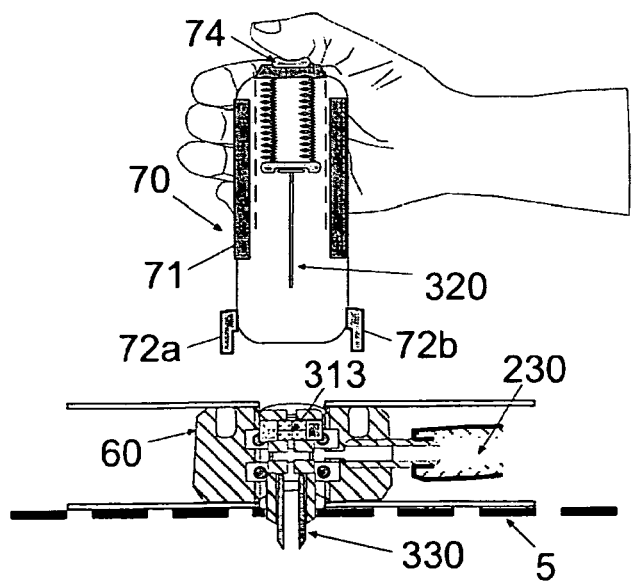

Once the penetrating cartridge (62) has been placed inside the well (60) and the cannula (330) has been lodged into the subcutaneous compartment under the skin (5), the inserter (70) is removed, as illustrated in FIG. 10d. A fluid communication is established with the fluid delivery tube (230) and the cannula (330) via the penetrating cartridge (62). The self-sealing septum (313) provides the requisite sealing of the penetrating cartridge (62) in order to prevent leakage of fluid and entry of contaminants.

FIGS. 11a-13c illustrate exemplary dispensing unit (10) being coupled to the skin (5) using a needle unit (20), according to some embodiments of the present invention. An exemplary embodiment of the needle unit (20) is disclosed in detail in co-pending/co-owned U.S. patent application Ser. No. 60/876,679, disclosure of which is incorporated herein by reference in its entirety.

In some embodiments, the needle unit (20) (also referred to as a cradle unit) includes two parts:

1. The cradle part provided with:
   a. A cradle base.
2. The penetrating cartridge part (also referred to as a cannula cartridge unit) includes:
   a. A well;
   b. A cannula; and,
   c. A penetrating member.

FIG. 11a is a side-view of an exemplary cradle part (21), according to some embodiments of the present invention. The cradle part (21) includes a cradle base (300), connecting latches (306a-d) (connecting latches 306a and 306d are shown in FIG. 11a), an opening (307), and anchoring latches (302a-d) (anchoring latches 302a and 302d are shown in FIG. 11a). The anchoring latches (302a-d) are disposed around a perimeter of the cradle base (300) and secure the dispensing unit (10) to the cradle part (21). The connecting latches (306a-d) are disposed around the opening (307) and secure the penetrating cartridge part (22) (shown in FIG. 11D) to the cradle base (300). In some embodiments, the latches (302a-d) and (306a-d) create a snap-fit locking arrangement between the latches and the dispensing unit (10) and the penetrating cartridge part (22), respectively.

Figure 11:
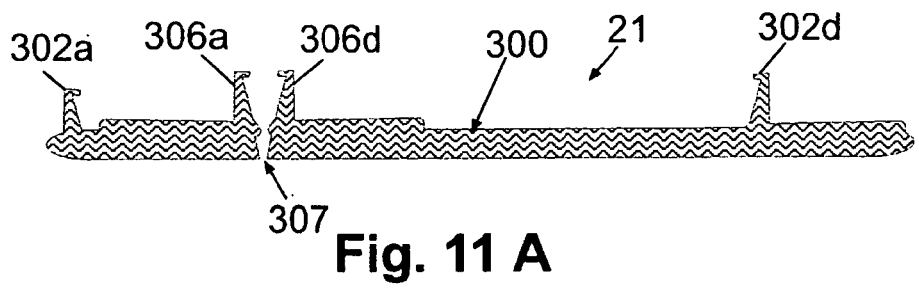
FIGS. 11a-d illustrate an exemplary needle unit, according to some embodiments of the present invention.
Figure 11B:
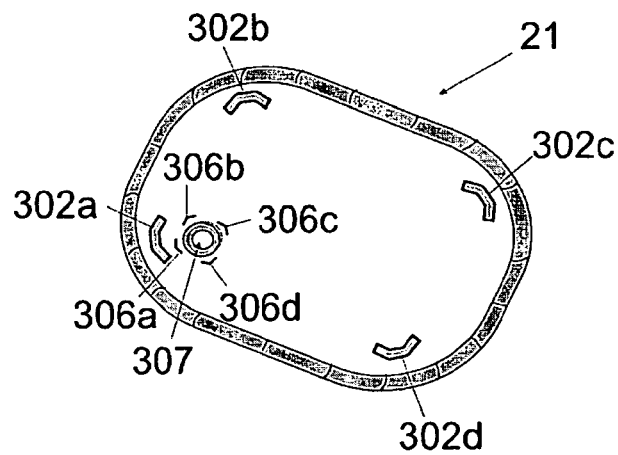
Figure 11C:
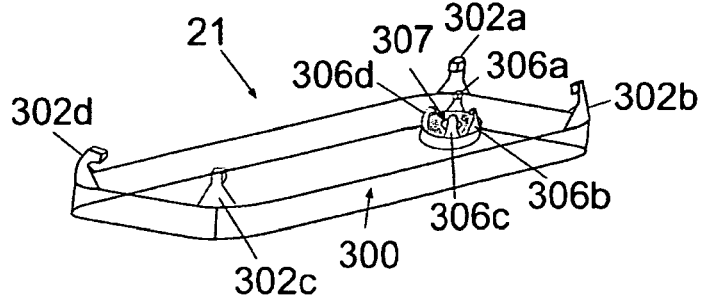

FIGS. 11b-c are a top view and a perspective view of the cradle part (21) shown in FIG. 11a. In some embodiments, the cradle base (300) can include a raised border that allows further stability to the inserted dispensing unit (10).

Figure 11D:
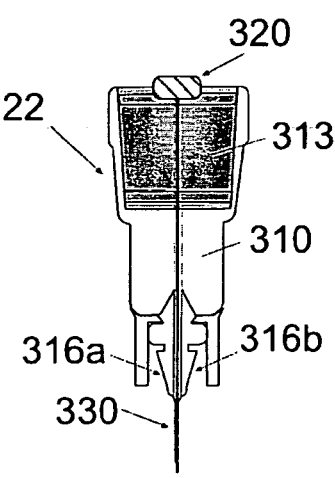

FIG. 11d shows the penetrating cartridge part (22), which is similar to the penetrating cartridge (62) discussed above and includes some of the similar components. The part (22) includes a well (310), lateral recesses (recesses 316a and 316b are shown in FIG. 11d), a septum (313), the cannula (330) and the penetrating member (320). The recesses (316a and 316b are shown in FIG. 11d) correspond to the latches (306a-d) and are configured to mate with the latches (306a-d) when the penetrating cartridge part (22) is connected to the cradle part (21), thereby anchoring of the penetrating cartridge part (22) to the cradle part (21). In an assembled state, the penetrating member (320) is inserted through the well (310) of the part (22) and the cannula (330). The septum (313) seals the well (310) to prevent fluid leakage and/or entry of contaminants.

Figure 12A:
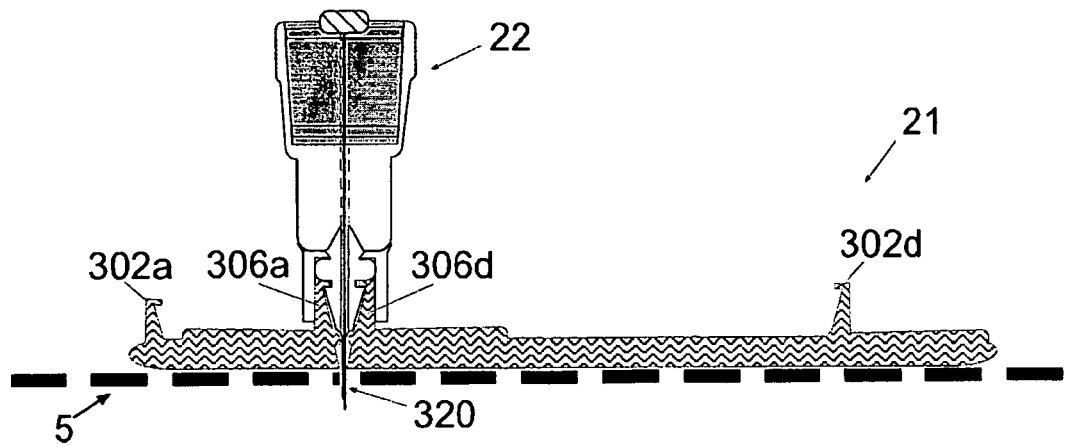
FIGS. 12a-b illustrate exemplary cannula insertion using the needle unit having a cradle part and a penetrating cartridge part, according to some embodiments of the present invention.
Figure 12B:
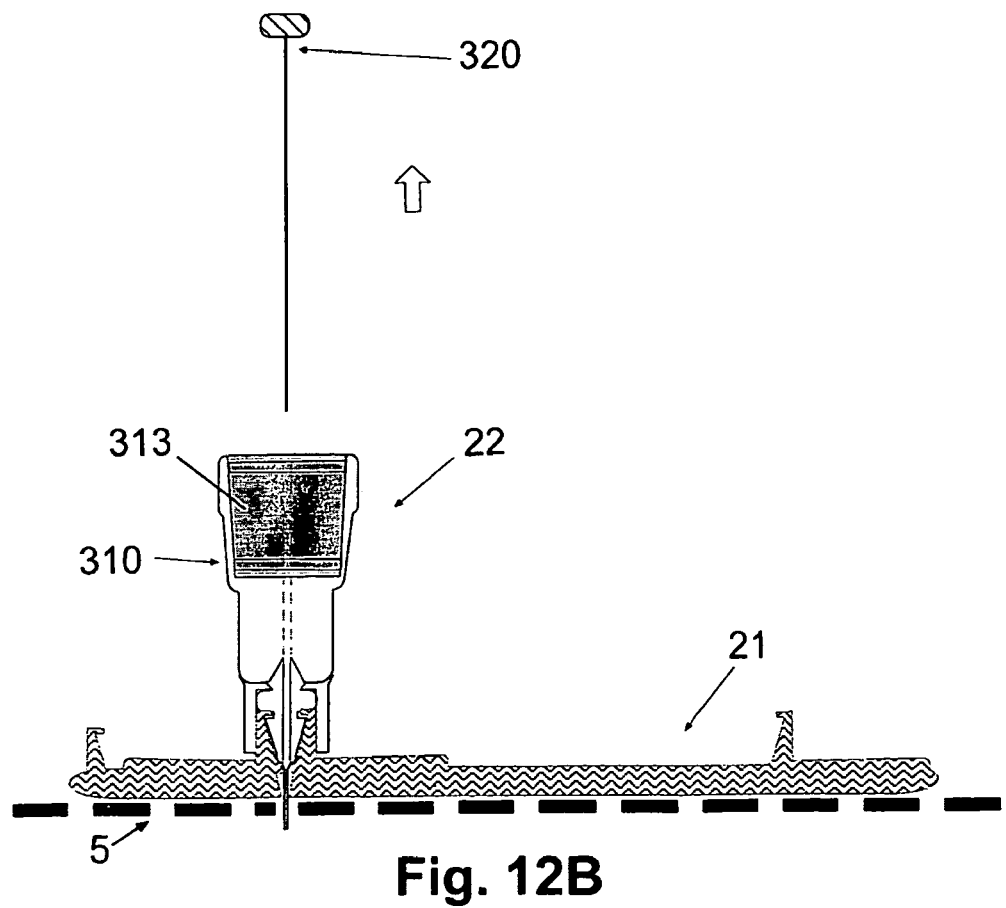

FIGS. 12a-b show exemplary connection of the cradle part (21) and the penetrating cartridge part (22), according to some embodiments of the present invention. The parts (21) and (22) are connected subsequent to the cradle part (21) being adhered to the skin (5) of the patient, as illustrated in FIG. 12a. The attachment to the skin (5) can be carried out using adhesives or any other means. As can be understood by one skilled in the art, an adhesive layer on the cradle part (21) faces the skin (5) immediately prior to being attached to the skin (5). Once the cradle part (21) is secured to the skin (5) and prior to the connection of the dispensing unit (10), an access to patient's subcutaneous compartment is established via penetrating cartridge part (22). Referring back to FIG. 12a, a connection of the penetrating cartridge part (22) to the cradle part (21) can be carried out using a combination of the latches (306a-d) and the recesses (316a-d). As can be understood by one skilled in the art, other ways to connect the parts (21) and (22) are possible. Once the parts (21) and (22) are secured to each other, the penetrating member (320) pierces the skin (5) and allows insertion of the cannula (330) into the subcutaneous compartment.

Subsequent to the insertion of the cannula (330), the penetrating member (320) can be removed. FIG. 12b shows removal of the penetrating member (320) from the penetrating cartridge part (22). After the penetrating member (320) is removed, the cradle part (21) remains adhered to the skin (5) and the cannula (330) remains inserted into the body. The self-sealable septum (313) seals off the well (310) and allows a connecting lumen (not shown in FIG. 12b) of the dispensing unit (10) to repetitively pierce the septum (313) for establishing fluid communication with the cannula (330) and the fluid delivery tube (230) (not shown). Thus, the dispensing unit (10) can be connected to and disconnected from the needle unit (20) as many times as desired. The self-sealable septum (313) prevents leaking of the dispensed fluid and entry of contaminants.

Figure 13A:
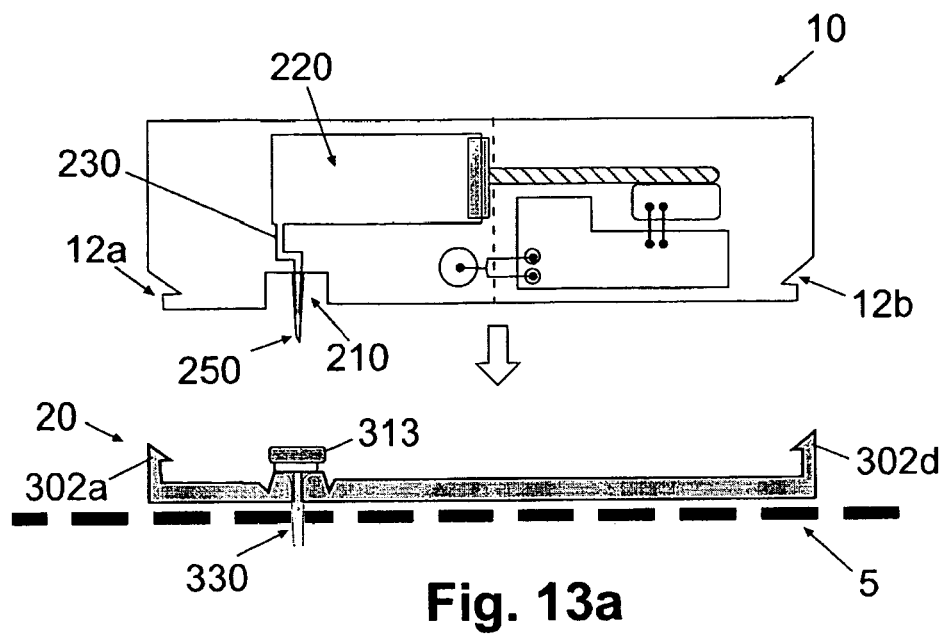
FIGS. 13a-c illustrate exemplary connection and disconnection of the dispensing unit to and from the needle unit, according to some embodiments of the present invention.
Figure 13B:
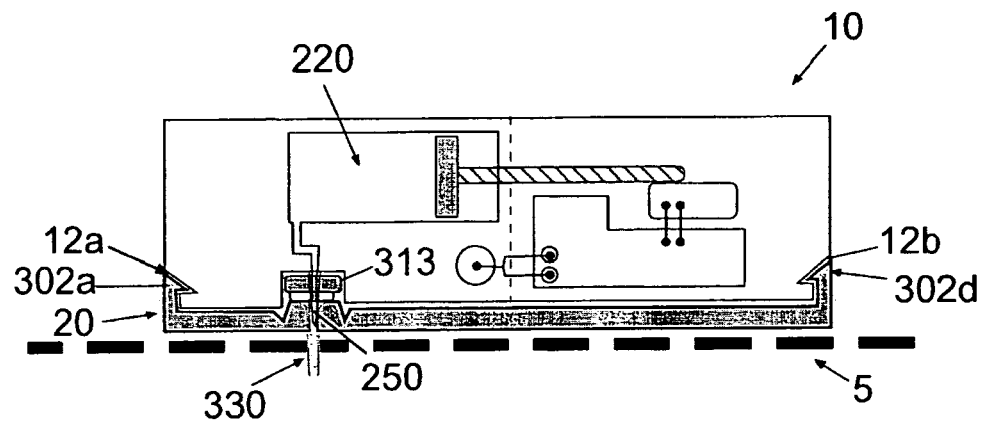

FIG. 13a shows exemplary connection of the dispensing unit (10) to the needle unit (20), according to some embodiments of the present invention. In order to connect with the needle snit (20), the dispensing unit also includes a connecting lumen (250). The connecting lumen (250) is in fluid communication with reservoir (220). The connecting lumen (250) is further disposed near the outlet port (210). In some embodiments, the outlet port (210) is configured as a recess in the housing of the dispensing unit (10) in order to accommodate receiving the penetrating cartridge part (22) which is placed into the opening (307) of the cradle base (300) (see, FIGS. 9a-12d). When the dispensing unit (10) is brought in close proximity to the needle unit (20), the connecting lumen (250) pierces the well's self-sealed rubber septum (313) and establishes a sealed fluid communication between the lumen (250) and the cannula (330), thereby allowing fluid communication between the cannula (330) and the reservoir (220). To secure the dispensing unit (10) to the cradle part (21), the dispensing unit (10) includes notches (12a-d) (notches 12a and 12b are shown in FIG. 13a) that are configured to mate with the anchoring latches (302a-d) of the needle unit (20). The connection of the dispensing unit (10) to the needle unit (20) is illustrated by an arrow in FIG. 13a. FIG. 13b shows the dispensing unit (10) attached to the needle unit (20) (and the dispensing unit being in an operating mode). As can be understood by one skilled in the art, connection of dispensing unit (10) to the needle unit (20) can be established using any other means.

Figure 13C:
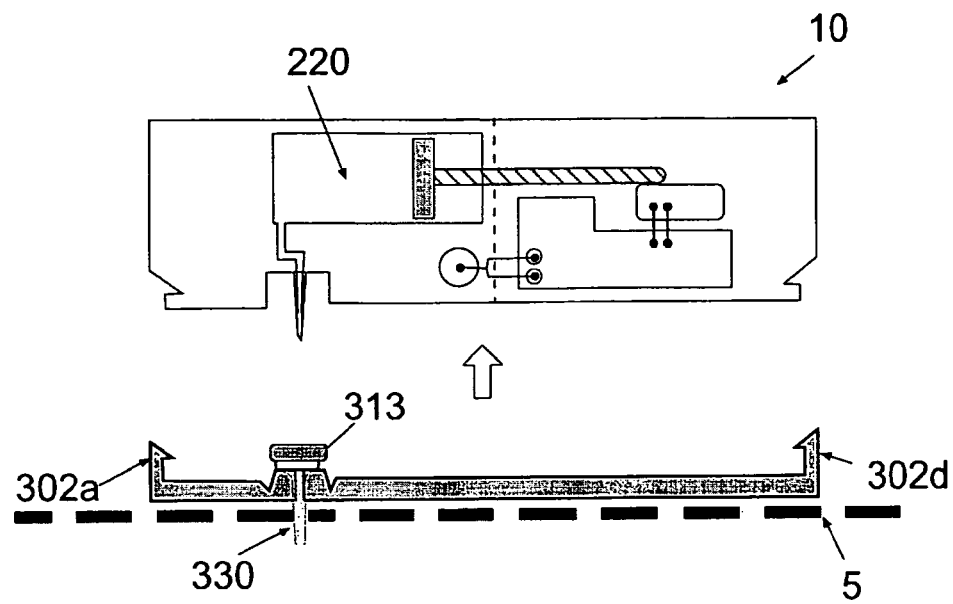

FIG. 13c shows disconnection of the dispensing unit (10) by pulling the elastically deformable latches (302a-d) backwards. Then, the dispensing unit (10) is pulled away from the needle unit (20), as indicated by the arrow in FIG. 13c. Subsequent to removal of the dispensing unit, the needle unit (20) continues to remain adhered to the skin (5) and the cannula (330) continues to remain in the subcutaneous compartment. The self-sealable septum (313) maintains a tight seal of the well (310) subsequent to removal of the dispensing unit (10), thereby preventing leakage of fluid and/or entry of contaminants.

Figure 14A:
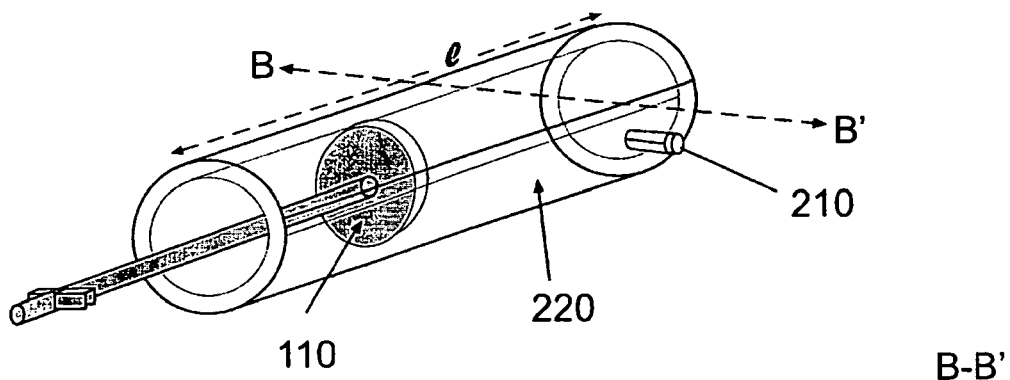
FIGS. 14a-b illustrate an exemplary reservoir having a round cross-section, according to some embodiments of the present invention.
Figure 14B:
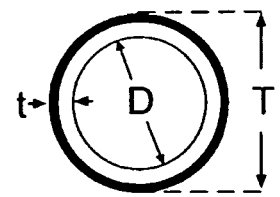
Figure 15A:
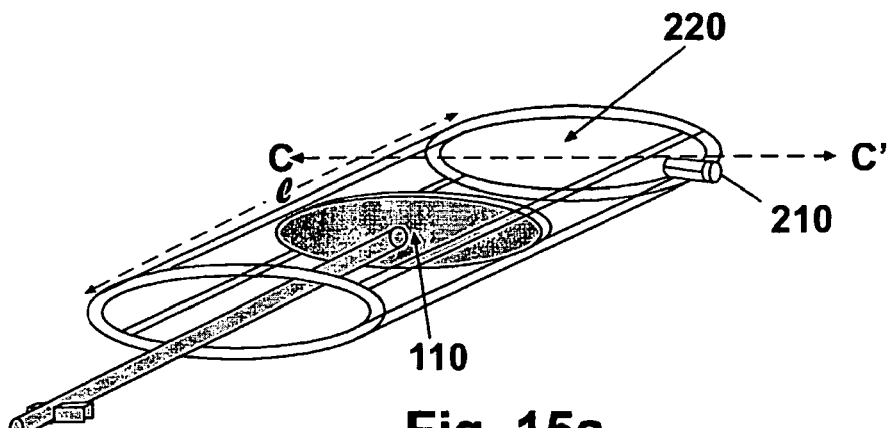
FIGS. 15a-b illustrate an exemplary reservoir having an elliptical cross-section, according to some embodiments of the present invention.
Figure 15B:
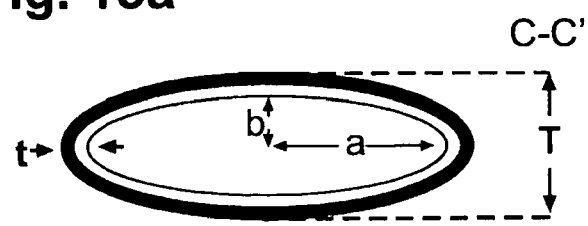
Figure 16A:
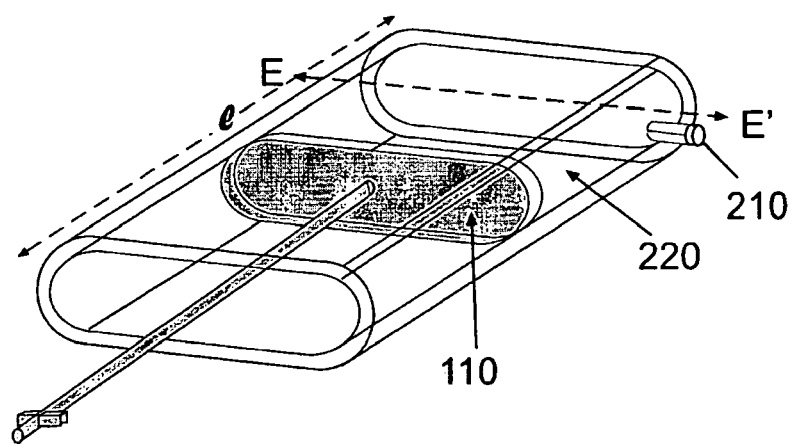
FIGS. 16a-b illustrate an exemplary reservoir having an oval cross-section, according to some embodiments of the present invention.
Figure 16B:
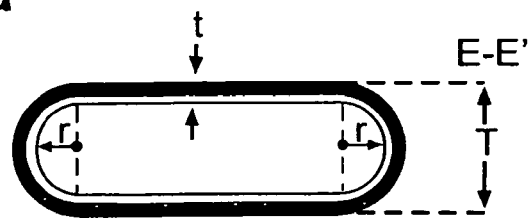

FIGS. 14a-16b illustrate exemplary reservoirs (220), according to some embodiments of the present invention. FIGS. 14a-b illustrate an exemplary reservoir (220) having a circular cross-section. FIGS. 15a-b illustrate an exemplary reservoir (220) having an oval cross-section. FIGS. 16a-b illustrate an exemplary reservoir (220) having a cross-section defined by several curves (e.g., 4-curves, 8-curves).

FIG. 14a shows a cylindrical reservoir (220) having a plunger (110). The reservoir (220) includes a hollow housing encompassed by reservoir walls. One end of the reservoir (220) is open and the other one is closed to prevent fluid leakage. The open end of the reservoir is enclosed by the plunger (110) thereby preventing leakage of fluid from the open end. As stated above, the plunger (110) is configured to slide back and forth inside the reservoir (220) to force the fluid from the outlet port (210) located on the housing of the reservoir (220). The reservoir (220) contains, for example, maximum 2 cubic centimeters ("cc") of fluid. It has a length (l) (that can be for example, about 18 mm), an internal diameter (D) (e.g., about 12 mm) and a wall thickness (t) (e.g., about 1 mm). In some embodiments, the plunger's height (T) is about 14 mm. FIG. 14b is a cross-sectional view of the reservoir (220). The cross-section is taken along the direction B-B' shown in FIG. 14a.

FIG. 15a illustrates an oval (or elliptical) reservoir (220) having a plunger (110). FIG. 15b is a cross-sectional view of the reservoir (220). The cross-section is taken along the direction C-C' designated in FIG. 15a. Some of the advantages of the oval or elliptical reservoir (220) are that it may reduce thickness of the reservoir and thereby allow the entire unit (10) (not shown) to have a slim profile.

FIG. 16a shows a reservoir (220) having elliptical cross-section. As above, the reservoir (220) is provided with the plunger (110). FIG. 16b shows a cross-sectional view of the reservoir (220). The cross-section is taken along the direction E-E' designated in FIG. 16a. As above, the plunger (110) has a matching cross-section as the interior portion of the reservoir (220).

The elliptic and oval configurations shown in FIGS. 15a-16b cause the reservoir (220) to have thin profile having a thickness of about 10 mm. The lengths of such reservoirs can be on the order of about 20 mm and reservoirs' capacities can be a maximum of 2 cc of fluid. As can be understood by one skilled in the art, the dispensing unit (10) fitted with such oval or elliptical reservoir will also have thin profile, thereby providing the patient with a comfortable and discreet pump unit.

Figure 17A:
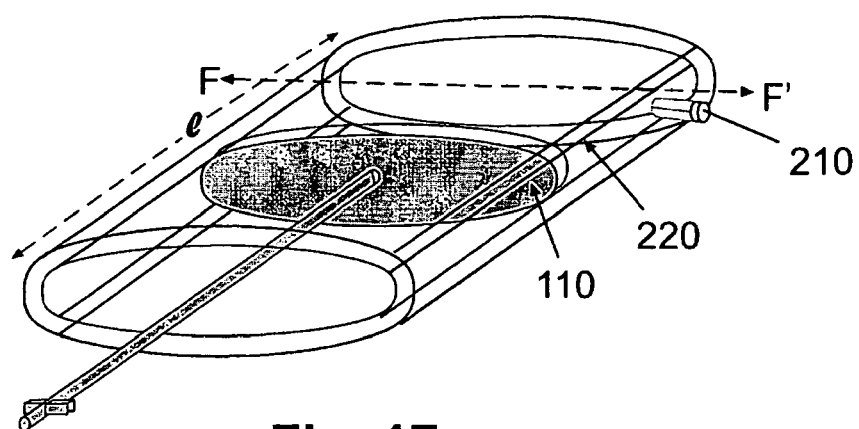
FIGS. 17a-b illustrate an exemplary reservoir having a cross-section defined by four curves, according to some embodiments of the present invention.
Figure 17B:
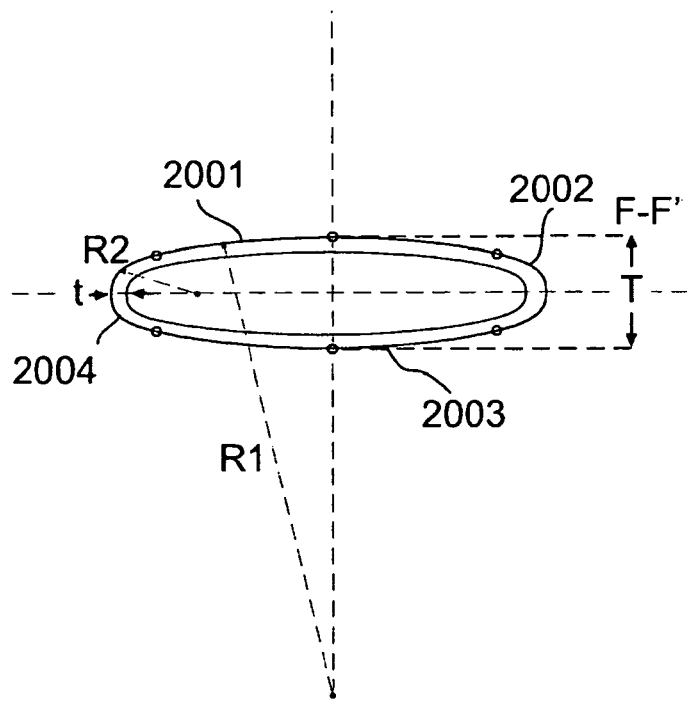

FIGS. 17a-b illustrate a multi-curve reservoir (220), according to some embodiments of the present invention. FIG. 17a is a perspective view of the multi-curve reservoir (220) and FIG. 17b is a cross-sectional view of the reservoir shown in FIG. 17a taken at line F-F'. The reservoir (220) is also fitted with the plunger (110). As shown in FIGS. 17a-b, the cross-section of the reservoir (220) is defined by four curvatures. Two of the curvatures (top curvature 2001 and bottom curvature 2003) have a radius R1 and two other curvatures (side curvatures 2002 and 2004) have a radius R2. A connection between each two adjacent curves is smooth. Such multi-curvature reservoir (220) provides additional rigidity to the reservoir (220) and at the same time allows maintaining of a thin profile of the reservoir (220). As can be understood by one skilled in the art, the reservoir (220) can have more than four curvatures defining its shape and that each curvature may have a different radius, length and width.

As can be understood by one skilled in the art, the dispensing unit (10) can have multiple reservoirs (220), where each reservoir can have different shapes, designs, and dimensions, such the ones shown in FIGS. 14a-17b.

Figure 18A:
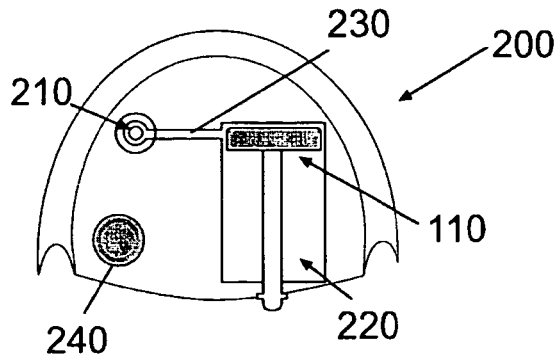
FIGS. 18a-b illustrate the disposable part containing an exemplary syringe-type reservoir, according to some embodiments of the present invention.
Figure 18B:
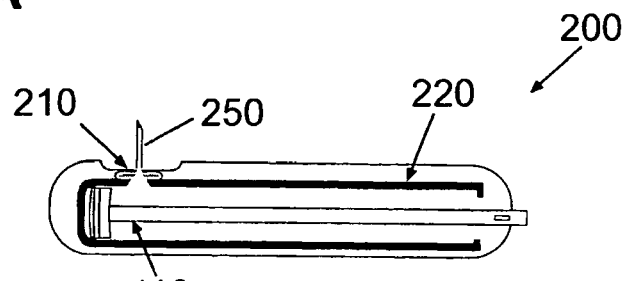
Figure 19A:
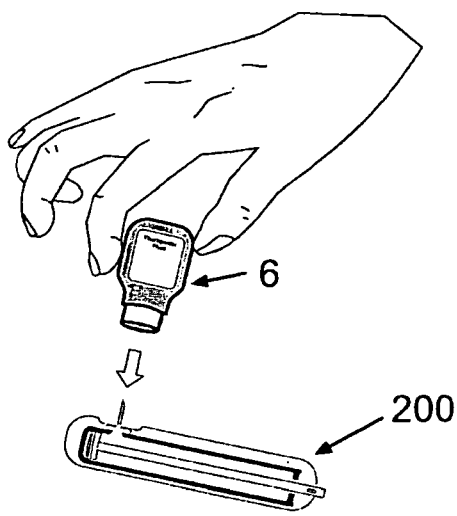
FIGS. 19a-f illustrate an exemplary filling of the reservoir and priming procedure, according to some embodiments of the present invention.
Figure 19B:
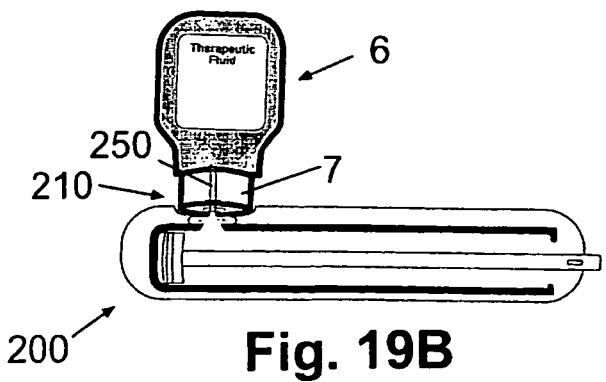
Figure 19C:
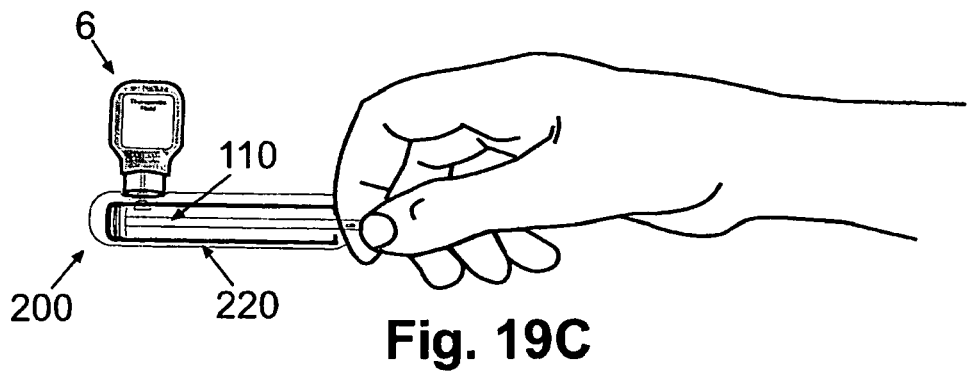
Figure 19D:
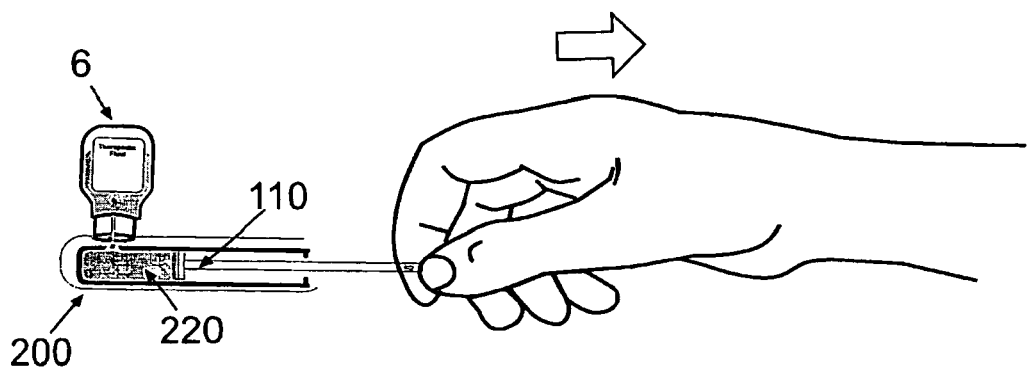
Figure 19E:
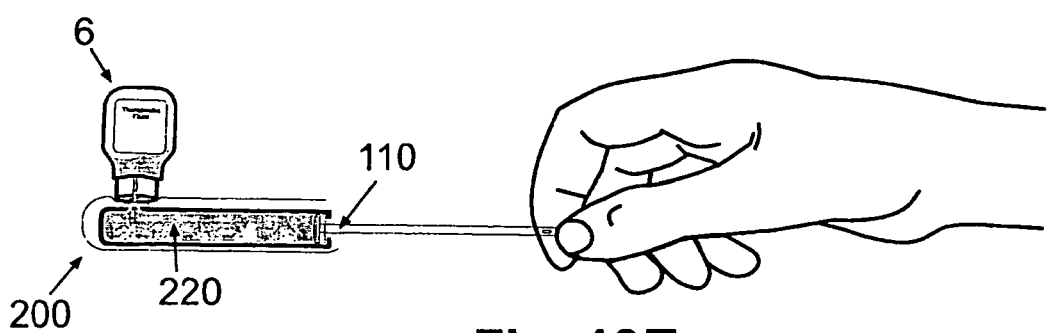
Figure 19F:
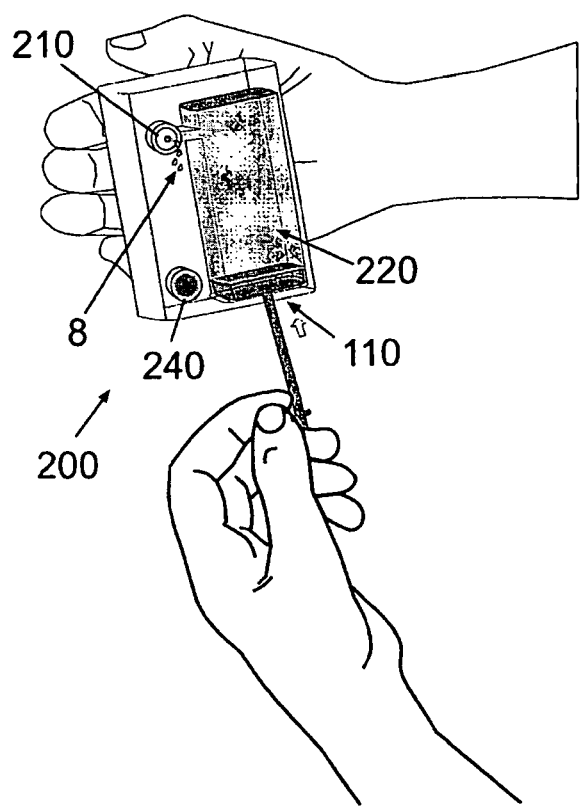

FIGS. 18a-19f illustrate filling and priming procedures of the reservoir (220), according to some embodiments of the present invention. Specifically, FIGS. 18a-19e illustrate the disposable part (200) during the filling procedure and FIG. 19f illustrates the disposable part 200 during priming procedure.

As shown in FIG. 18a, the disposable part (200) includes the reservoir (220) having the plunger (110), the fluid delivery tube/tubular connector (230), the battery (240) and the outlet port (210). The disposition and connection of these components has been described above. As further illustrated in FIG. 18a, the disposable part (200) (and hence, the dispensing unit (10)) can have an oval or an elliptical profile. FIG. 18b is a transverse cross-sectional view of the disposable part (200) shown in FIG. 18a. As further shown in FIG. 18b, the outlet port (210) of the disposable part (200) includes the connecting lumen (250). The connecting lumen (250) is in fluid communication with the reservoir (220) via the fluid delivery tube (230). As stated above, the connecting lumen (250) allows fluid communication between the reservoir (220) and components connected to the lumen (250). In this case, the lumen (250) is used for delivery of the fluid from a filling container to the reservoir (220). Prior to filling the reservoir (220), the plunger (110) is pushed all the way into the reservoir (220) so that the plunger's shaft is substantially inside the reservoir, as illustrated in FIGS. 18a-b.

A therapeutic fluid container (6) (e.g., containing insulin) is connected to the disposable part (200) at the outlet port (210), as illustrated in FIGS. 19a-b. Specifically, the connecting lumen (250) pierces the container's septum (7) thereby allowing fluid transfer from the container (6) to the reservoir (220). The fluid is drawn from the container (6) by pulling on the shaft of the plunger (110) and, thus, creating a suction effect thereby drawing the fluid from the container (6), as illustrated in FIGS. 19c-e. The amount of fluid (i.e., insulin) filled into the reservoir (220) can be tailored to the patient's needs, i.e., a child can fill only a portion of the reservoir (220) because the total daily dose is relatively small; while an adult can use the entire volume of reservoir (220). Thus, by virtue of the above-described configuration of the reservoir and the disposable part there is no need to supply customized reservoirs (220) and there is almost no wasted fluid. In some embodiments, the patient/user may observe the fluid being filled into the reservoir (220) during the filling procedure.

FIG. 19f illustrates an exemplary priming procedure of the reservoir (220), according to some embodiments of the present invention. The priming procedure is designed to purge any air that may be accumulated in the reservoir (220) after removal of the container (6). Air bubbles are purged by holding the disposable part (200) in an upright position and slightly pressing the plunger (110) forward until fluid (8) is dripping from the outlet port (210).

In some embodiments, the reservoir (220) may reside within the disposable part being retained in an external housing. Such housing can be made at least partially from a transparent material to allow the patient to continuously monitor level/content of fluid in the reservoir (220).

Figure 20A:
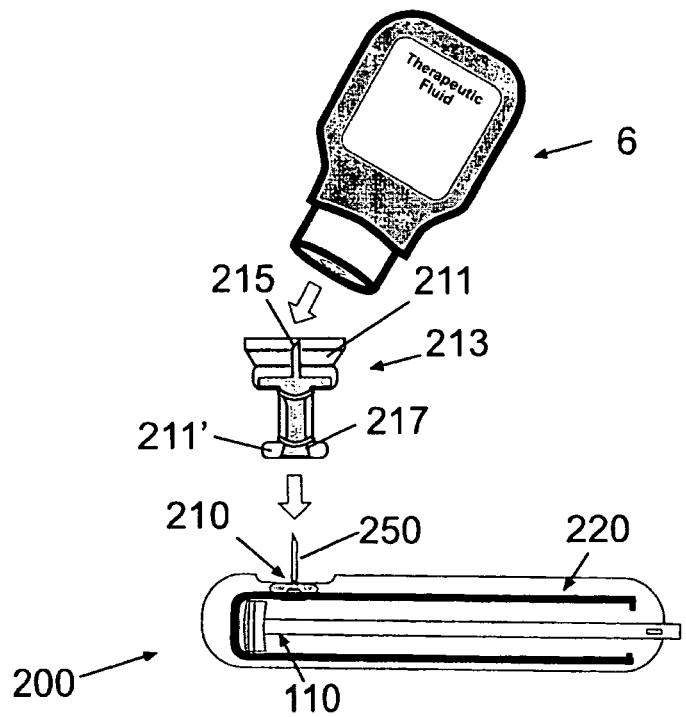
FIGS. 20a-b illustrate an exemplary filling of reservoir using an adaptor, according to some embodiments of the present invention.
Figure 20B:
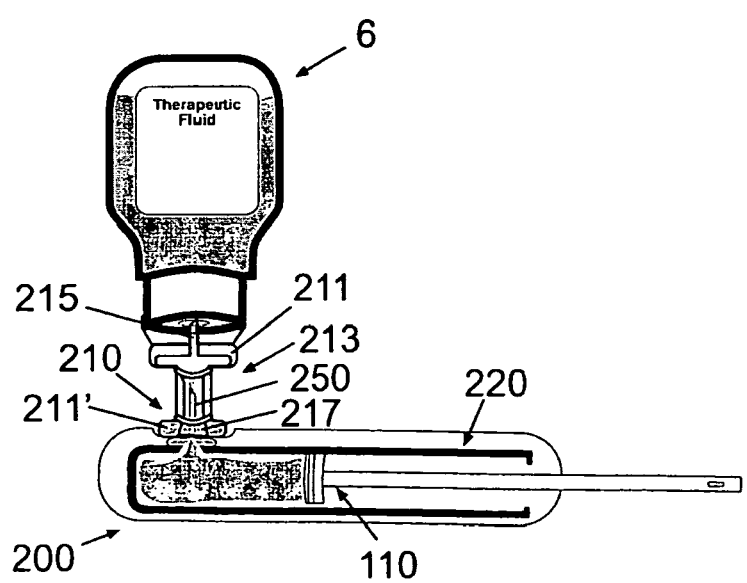

In some embodiments, the filling procedure of the reservoir (220) can be carried out using an auxiliary adaptor (213), as shown in FIGS. 20a-b. FIG. 20a shows an exemplary adaptor (213) that includes two opposite ports: one port (211) for connection with the container (6) and the other port (211') for communication with the reservoir (220). The port (211) includes a needle (215), which upon connection with the container (6) pierces the container's septum (7). The adaptor (213) further includes a rubber septum (217) sealing the port (211'). The septum (217) is pierced by the connecting lumen (250) when the adaptor (213) is coupled to the outlet port (210) for fluid transfer purposes. FIG. 20b shows connection of the adaptor (213) to the disposable part (200) and to the container (6). As shown, the container (6) is coupled to the port (211) of the adaptor (213) whereas the port (211') of the adaptor (213) is coupled to the port (210) of the disposable part (200). Once the above connections are made, therapeutic fluid is transferred from the container (6) through the adaptor (213) and into the reservoir (220), thereby filling the reservoir (220) with the fluid. The filling procedures are similar to the filling procedures discussed in connection with FIGS. 18a-19e above. In some embodiments, the reservoir (220) can be filled using an auxiliary syringe connected to an inlet port (not shown in FIGS. 20a-b).

After filling the reservoir (220), the reusable part (100) and the disposable part (200) can be connected to each other thereby creating the dispensing unit (10), as discussed above. The dispensing unit (10) can then be attached to the skin of the patient, as shown for example in FIGS. 13a-c.

Figure 21A:
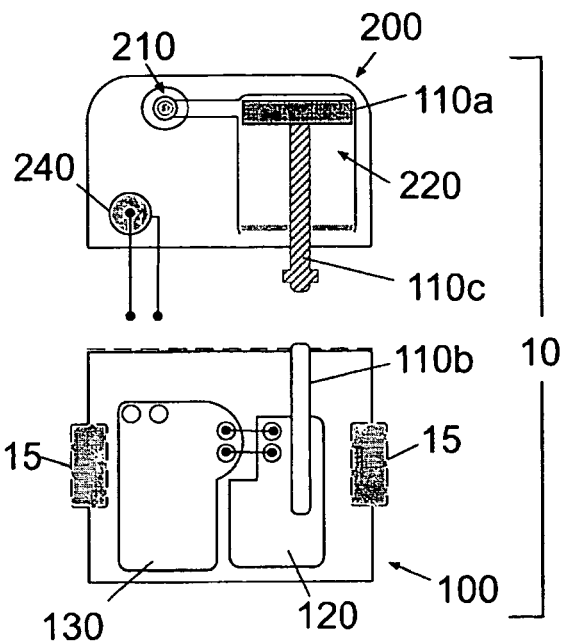
FIGS. 21a-e illustrate an exemplary connection of the disposable and reusable parts while the plunger is shared by the reusable and disposable parts, according to some embodiments of the present invention.

FIGS. 21a-e and 22a-c illustrate exemplary disposable part (200) and reusable part (100) having a rod (110b) of the plunger (110) disposed in both parts, according to some embodiments of the present invention. As illustrated in FIG. 21a, the plunger (110) includes a plunger head (110a) and the plunger rod (110b). The plunger head (110a) is coupled to the plunger rod (110b). The plunger rod (110b) is coupled to the driving mechanism (120) that allows movement of the plunger (110) between the reusable part (100) and the disposable part (200). The movement of the plunger rod (110b) causes movement of the plunger head (110a) inside the reservoir (220). The plunger rod (110b) can be coupled to a driving gear (not shown) disposed inside the driving mechanism (120). Further, the movement of the plunger (110) can be controlled by electronic components (130) (e.g., controller) sending appropriate commands to the driving mechanism (120). The movement of the plunger (110) can be based on a particular fluid delivery schedule/rate (e.g., basal vs. bolus doses).

In some embodiments, the dispensing unit (10) can also include an auxiliary rod (110c), which can be used for filling the reservoir (220), as shown in FIG. 21a. Once the reusable and disposable parts are disconnected from one another for the purpose of filling the reservoir (e.g., the user/patient received an indication or determined that the reservoir is substantially empty), the plunger rod (110b) can be disconnected from the plunger head (110a) either automatically or manually and the auxiliary rod (110c) can be coupled to the plunger head (110a). The auxiliary rod (110c) can be connected to the plunger head (110a) either via a snap-fit arrangement, by screwing the rod (110c) to the plunger head (110a), or using any other suitable means.

Figure 21B:
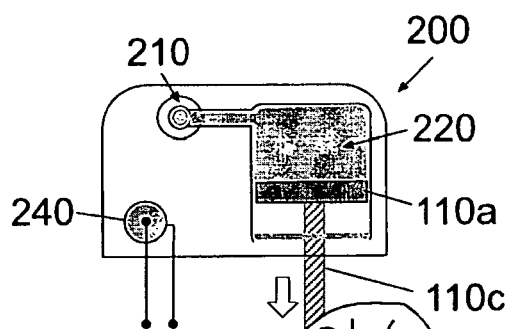
Figure 21C:
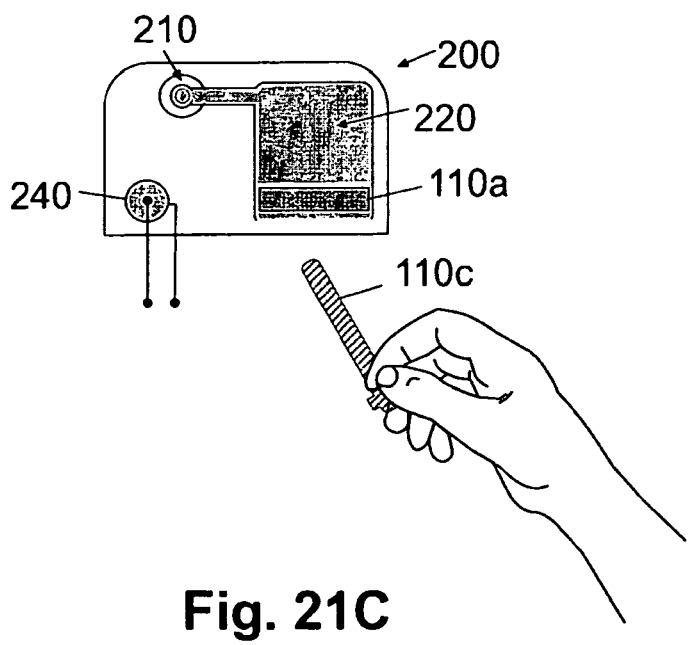

FIG. 21b shows disposable part (200) being disconnected from the reusable part (100) and the auxiliary rod (110c) being coupled to the plunger head (110a) while the reservoir (220) is being filled with therapeutic fluid. To fill the reservoir, the user/patient follows a similar procedure described above with regard to FIGS. 18a-19e. In this embodiment, the user pulls on the auxiliary rod (110c) away from the reservoir (220) as indicated by the arrow in FIG. 21b. As the user is pulling on the auxiliary rod (110c), the fluid is being drawn from the container (6) (not shown in FIG. 21b). Once the filling procedure is completed, the auxiliary rod (110c) is detached from the plunger head (110a) and removed from the disposable part (200), as shown in FIG. 21c. Further, upon filling the reservoir (220), the plunger head (110a) can approach a connection border between the reusable and disposable parts.

Figure 21D:
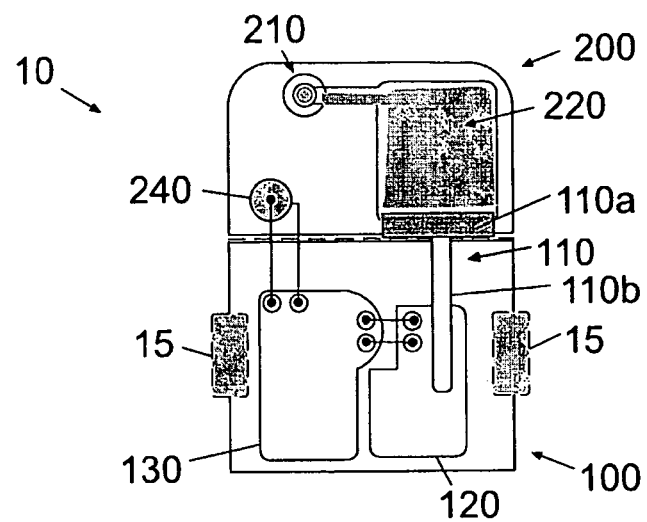
Figure 21E:
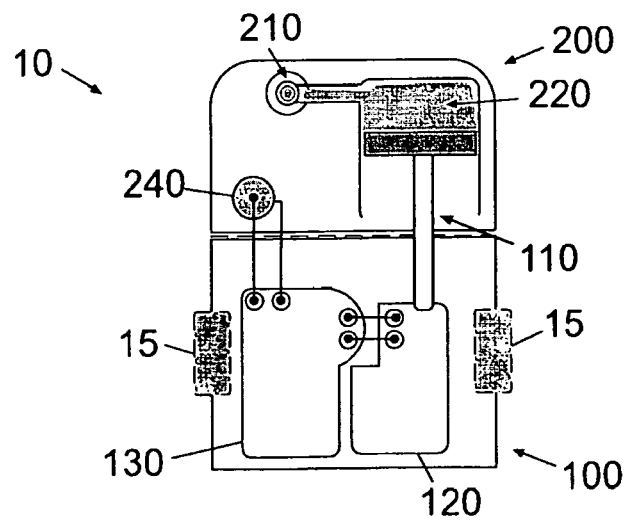

Once the auxiliary rod (110c) is removed, the reusable and disposable parts can be connected to each other, as illustrated in FIG. 21d. Upon connection of the two parts the distal end (the end away from the driving mechanism and proximal to the plunger head (110a)) of the plunger rod (110b) is affixed to the plunger head (110a); whereas the proximal end (the end coupled to the driving mechanism (120)) is engaged with the driving mechanism (120). The driving mechanism (120) causes positive displacement of the plunger rod (110b) inside the reservoir (220) subsequent to receiving appropriate commands from the controller and being powered by the batteries (240). FIG. 21e shows the dispensing unit (10) in operation. Upon application of the driving mechanism (120), the plunger (110) is displaced within the reservoir (220) and pushes the fluid toward the outlet port (210), thereby causing delivery of the fluid to the patient. As stated above, such delivery can be in various doses (e.g., bolus, basal, etc.) and can be preprogrammed into the controller by the user/patient, a computer, a remote control (40) (not shown), and/or any other device.

Figure 22A:
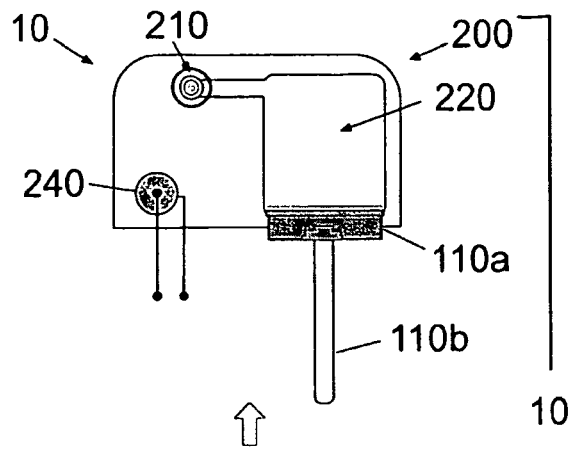
FIGS. 22a-c illustrate an exemplary connection of the disposable and reusable parts while plunger is located in the disposable part, according to some embodiments of the present invention.
Figure 22A:
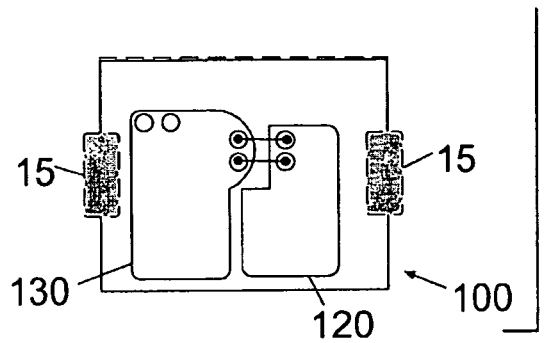
Figure 22B:
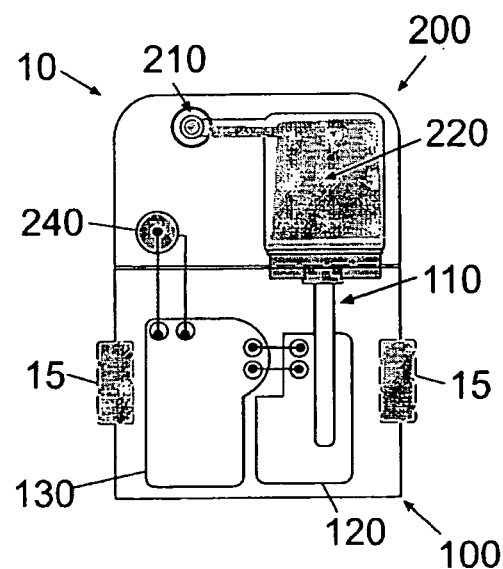
Figure 22C:
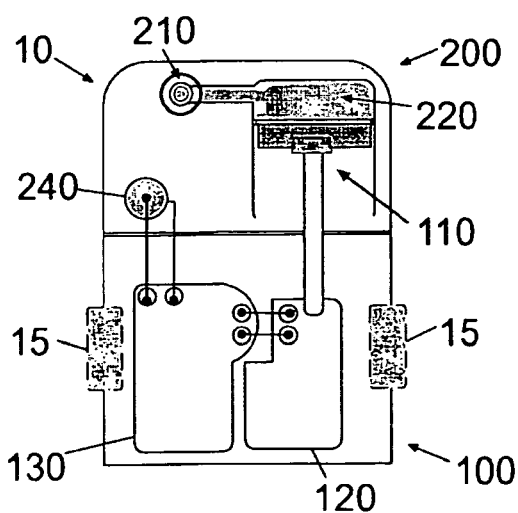

FIGS. 22a-c show another exemplary dispensing unit (10) having two parts, according to some embodiments of the present invention. In this embodiment, the plunger (110) is located within the disposable part (200) and can be detached from the driving mechanism (120) disposed in the reusable part (100). FIG. 22a shows the dispensing unit (10) prior to connection of the parts (100) and (200). The plunger (110) shown in FIGS. 22a-c includes same components as the plunger (110) shown in FIGS. 21a-e. Referring to FIG. 22a, the plunger head (110a) and plunger rod (110b) are coupled to each other and are both located in the disposable part (200), where the plunger head (110a) is disposed inside the reservoir (220) and the plunger rod (110b) is disposed outside the reservoir (220). The reservoir (220) can be filled using procedures that are similar to those described in connection with FIGS. 18a-19e. In this case the user/patient can pull on the plunger rod (110b) to fill the reservoir (220) rather than attaching the auxiliary rod (110c).

Once the parts (100) and (200) are connected to each other and the reservoir (220) is filled, the plunger rod (110b) can be engaged with the driving mechanism (120). Such engagement can be done via a snap-fit arrangement, screwing, ball-and-socket arrangement, or using any other suitable way. When the electrical connection(s) between the battery (240), and the electronic components/PCB (130) are established, the driving mechanism (120) can apply force to the plunger rod (110b), which in turn, applies force on the plunger head (110a), thereby pushing the fluid out of the reservoir (220) and toward the outlet port (210), as illustrated in FIG. 22b.

FIG. 22c shows further operation of dispensing unit (10). As the plunger (110) moves in a forward positive direction, the fluid in the reservoir (220) flows via the fluid delivery tube (230) toward the outlet port (210), thereby delivering fluid to the patient. The filling and emptying of the reservoir can be continuously repeated (or repeated a specific number of times).

Figure 23A:
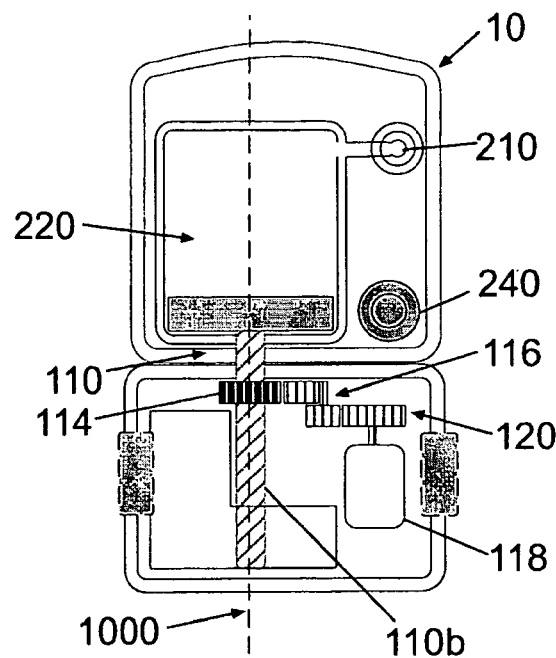
FIGS. 23a-b illustrate the dispensing unit having an exemplary driving mechanism fitted with a threaded rod and with a screw-nut for plunger displacement, according to some embodiments of the present invention.

FIGS. 23a-26c show exemplary alternatives for plunger (110) displacement using the driving mechanism (120), according to some embodiments of the present invention. FIG. 23a is a top cross-sectional view of the dispensing unit (10) having the reusable part (100) and disposable part (200) connected together. The unit (10) includes the plunger (110) having a threaded rod (110b) and a screw-nut (114) coupled to the threaded rod (110b). The screw-nut (114) is disposed within the reusable part (100) and is fixed, i.e., it does not move along axis (1000). The threaded rod (110b) and the screw-nut (114) are aligned along axis (1000), as shown in FIG. 23a. The threaded rod (110b) is capable of moving inside the screw-nut (114). The screw-nut (114) is further coupled to a gear (116), where the gear (116) is being part of the driving mechanism (120). The gear (116) is further fitted with at least one cogwheel. The gear (116) is driven by a motor (118) (e.g., a DC motor, a stepper motor, etc.), which is also part of the driving mechanism (120). In some embodiments, the gear (116) is connected to the motor (118) via a shaft or any other means allowing the motor (118) to rotate gear (116).

Figure 23B:
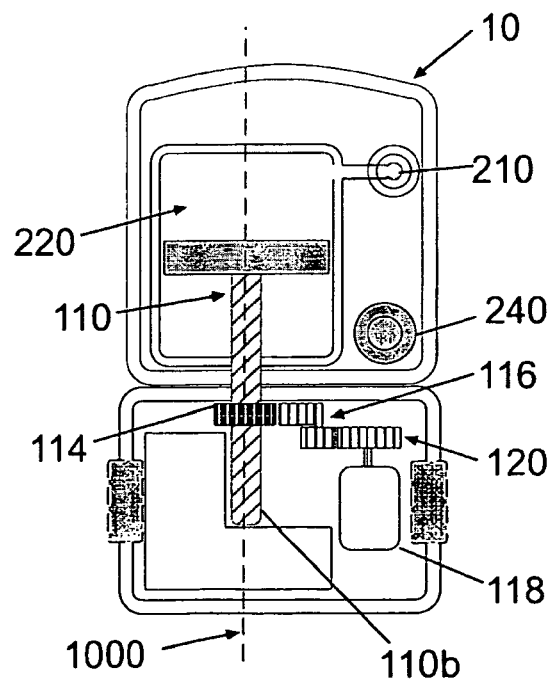

FIG. 23b shows the plunger (110) being displaced along axis (1000). During operation of the motor (118), the motor (118) rotates the gear (116). Rotational motion of the gear (116) is translated to the cogwheel coupled to the screw-nut (114) causing the screw-nut (114) to rotate. Since the threaded rod (110b) is inserted into the screw-nut (114), rotation of the screw-nut (114) translates the rod (110b), and thereby the plunger (110), along the axis (1000). Such translational movement of the plunger (110) displaces the fluid inside the reservoir (220) towards the outlet port (210). In some embodiments, the screw-nut (114) may serve as a cogwheel, thereby reducing the number of components in gear (116). As can be understood by one skilled in the art, the motor (118) can rotate in any direction, thus, causing the screw-nut (114) to rotate in various directions (according to the direction of rotation of the motor (118)). As such, the threaded rod (110b) can rotate in corresponding directions as well as translate back and forth along axis (1000), causing the plunger (110) to move in and out of the reservoir (220). As stated above, such movement is controlled by the controller (not shown) powered by the battery (240) and can be automatic based on a pre-programmed schedule or manual (e.g., upon pressing buttons (15)).

Figure 24A:
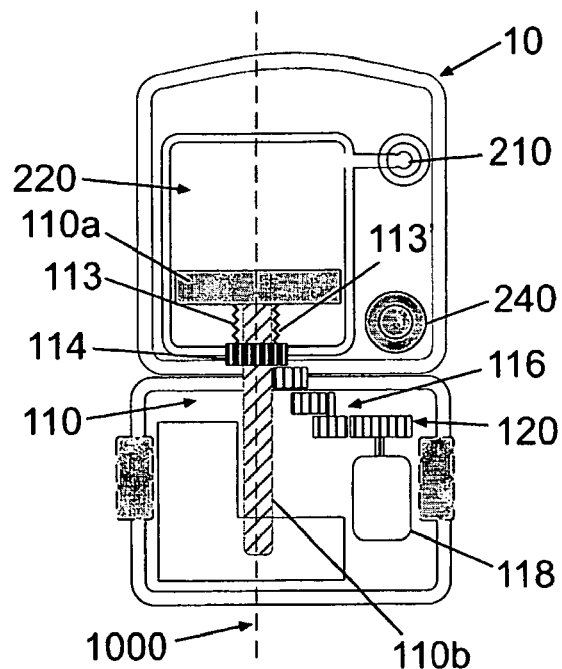
FIGS. 24a-b illustrate the dispensing unit having an exemplary driving mechanism fitted with a threaded rod, with a screw-nut and with driving springs for plunger displacement, according to some embodiments of the present invention.

FIG. 24a shows another exemplary dispensing unit (10), according to some embodiments of the present invention. The dispensing unit (10) includes the driving mechanism (120) having the threaded rod (110b) loaded with driving springs (113) and (113'), and the screw-nut (114) driven by the motor (118) and the gear (116). In some embodiments, the screw-nut (114) can be disposed in the disposable unit (200) and can be coupled to the gear(s) (116) upon connection of the reusable part (100) and disposable part (200). Alternatively, the screw nut (114) can be disposed inside the reusable part (100). Similar to the embodiment shown in FIGS. 23a-b, the screw-nut (114) is fixed and does not move along the axis (1000). The screw-nut (114) is further coupled to the gear(s) (116), which are rotated by the motor (118). Rotational motion of the gear(s) (116) is translated to the screw-nut (114) (via interaction of ratchet teeth on the screw-nut (114) and the gear(s) (116)). The driving springs (113), (113') are disposed between the screw-nut (114) and the plunger head (110a) and apply additional force to the plunger head (110a) during motion inside the reservoir (220). When the reservoir (220) is either being filled or is full, the springs (113) are in the compressed state.

Figure 24B:
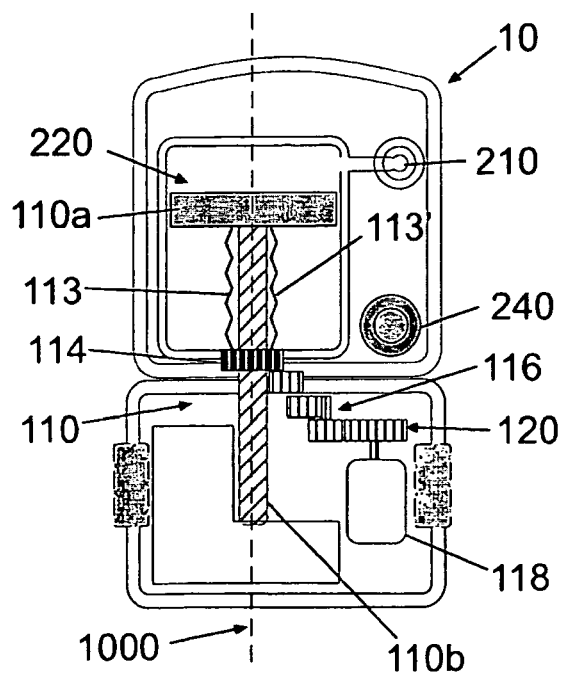

FIG. 24b shows the dispensing unit (10) during fluid dispensing procedure. The motor (118) rotates gear(s) (116), which cause rotation of the screw-nut (114) and translation along the axis (1000) of the threaded rod (110b) forward. The driving springs (113), (113') expand and apply additional force on the plunger head (110a). Application of additional force reduces torque that should be produced by the motor (118) in order to translate the plunger (110) inside the reservoir (220).

Figure 25A:
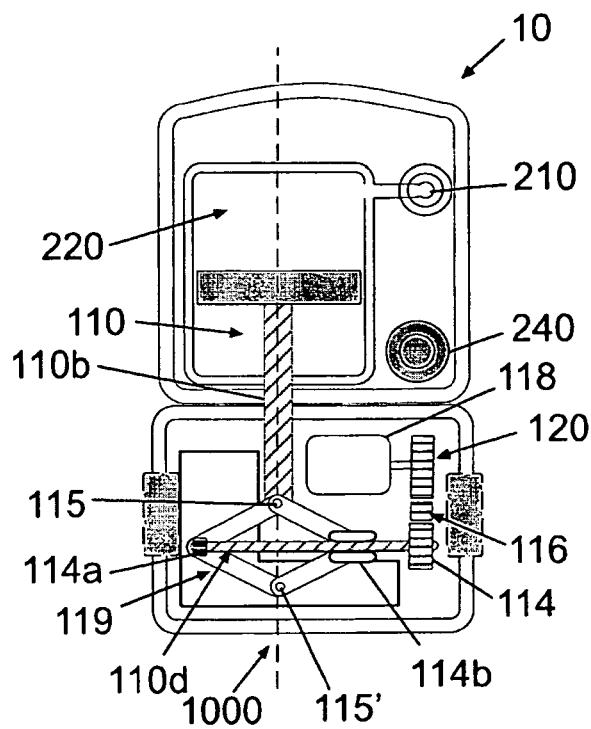
FIGS. 25a-b illustrate the dispensing unit having an exemplary driving mechanism fitted with a threaded rod, with a screw-nut and with lever bars for plunger displacement, according to some embodiments of the present invention.
Figure 25B:
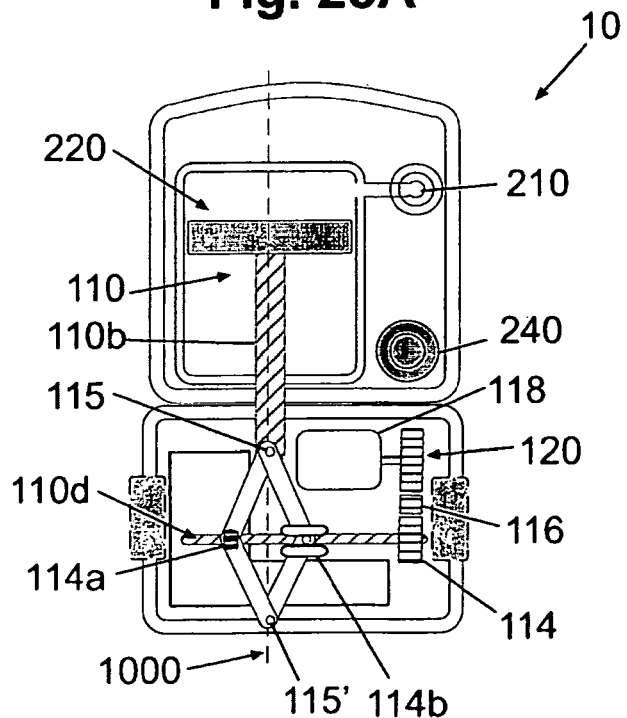

FIGS. 25a-b show another exemplary dispensing unit (10) having the driving mechanism (120). The driving mechanism (120) includes gear(s) (116), an auxiliary gear (114'), auxiliary screw-nuts (114a) and (114b), four hinged bars (119), a rod (110b), and a threaded rod (110d). The motor (118) of the driving mechanism (120) drives rotation of the gear(s) (116), which in turn rotate the auxiliary gear (114'). The auxiliary gear (114') is coupled to the threaded rod (110d). The threaded rod (110d) rotates in the same direction as the auxiliary gear (114'). The auxiliary screw-nuts (114a) and (114b) are threadedly secured to the threaded rod (110d), i.e., the screw-nuts (114a) and (114b) are configured to translate back and forth along the threaded rod (110d) as the rod (110d) rotates. The threaded rod (110d) includes threads that interact with the threads of the screw-nuts (114a) and (114b). The threads on the screw-nuts (114a) and (114b) are disposed in opposite directions with regard to each other to allow the screw-nuts (114a) and (114b) to translate along the rod (110d) in opposite directions with regard to each other. The hinged bars (119) are hingedly secured to the rod (110b) at pivot joint (115) and another pivot joint (115'), located on the opposite side of the threaded rod (110d), as illustrated in FIG. 25a.

The nuts (114a) and (114b) are also joined to the bars (119), thereby forming hinged pivots for the bars (119). Thus, the bars (119) have four hinged pivots that allow vertical and horizontal movement of the bars (119) during translational movement of the nuts (114a) and (114b). As stated above, when the auxiliary gear (114') is rotated by the motor (118) and gear(s) (116), the auxiliary gear (114') rotates the threaded rod (110d), such that the screw-nut (114a) is linearly displaced along the threaded rod (110d). The screw-nut (114b) also translates along the threaded rod (110d), as shown in FIG. 25b.

Hence, when screw-nuts (114a) and (114b) approach each other, the joints (115), (115') are displaced in opposite directions with respect to each other along the axis (1000), thereby forcing movement of the plunger rod (110b), and hence the plunger (110), toward the outlet port (210) and displacing fluid within the reservoir (220). In some embodiments, a reverse rotation of the auxiliary gear (114') forces reverse movement of the plunger (110) away from the outlet port (210). The reverse movement of the auxiliary gear (114') causes pivots (115) and (115') to move toward each other along axis (1000). This configuration reduces the overall length of the driving mechanism (120) along the axis (1000), thereby reducing the overall length of the dispensing unit (10).

Figure 26A:
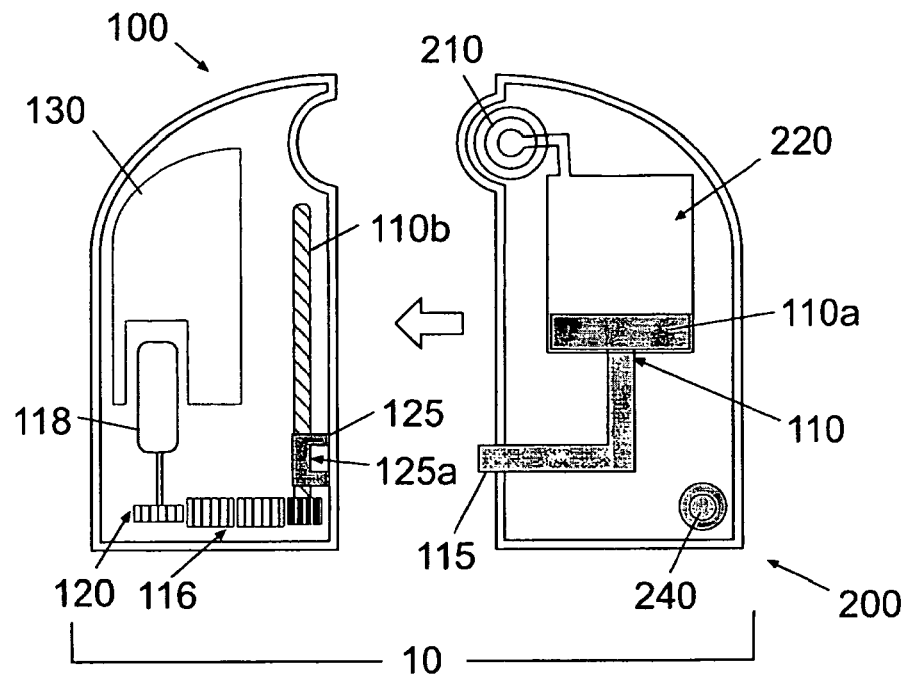
FIGS. 26a-c illustrate the dispensing unit having an exemplary driving screw nut and a plunger, according to some embodiments of the present invention.
Figure 26B:
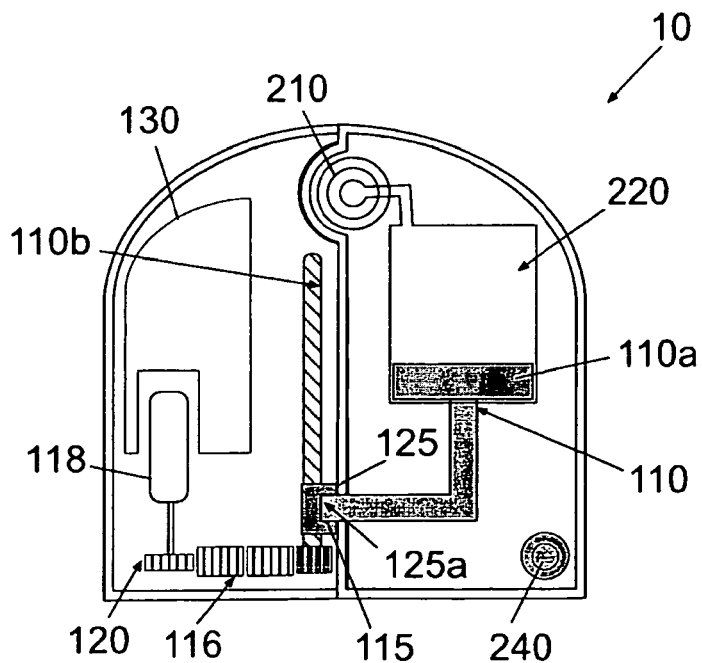
Figure 26C:
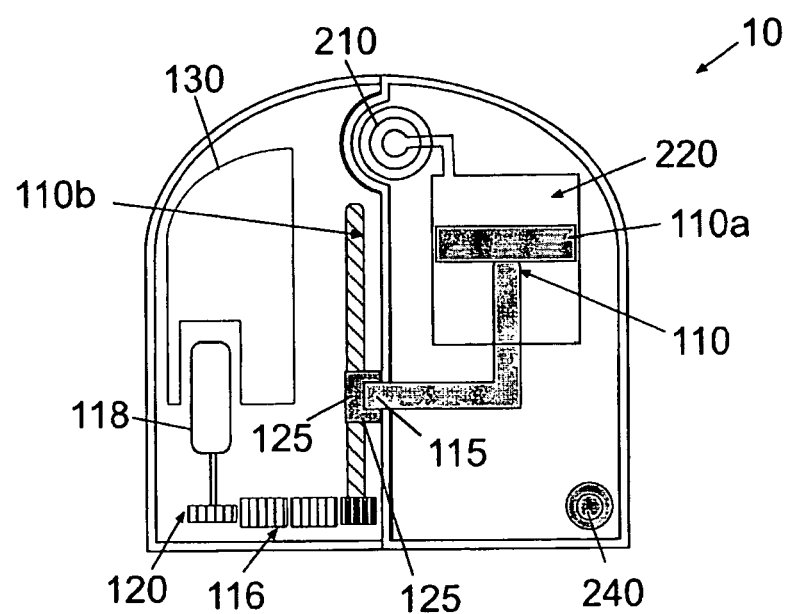

FIGS. 26a-c show another exemplary embodiment of the dispensing unit (10) having the disposable part (200) and reusable part (100), where the reusable part (100) includes a threaded rod (110b) and a driving screw-nut (125) coupled to the threaded rod (110b). The disposable part (200) includes a plunger (110) configured as an L-shaped rod with connecting end (115). The L-shaped rod (110) includes one longer section perpendicular to another shorter section. The driving screw-nut (125) includes a lateral recess (125a) configured to receive the connecting end (115) of the L-shaped rod, as illustrated in FIGS. 26a-b. The driving screw-nut (125) includes threads that are configured to mate with the threads disposed on the rod (110b). Thus, during rotation of the threaded rod (110b) (caused by the motor (118) and gear (116) of the driving mechanism (120)), the driving screw-nut (125) translates along the threaded rod (110b).

During operation, linear translation of the driving screw-nut (125) along the threaded rod (110b) causes simultaneous displacement of the plunger head (110a), thus urging fluid in the reservoir (220) towards the outlet port (210), as shown in FIG. 26c. The L-shaped rod allows more compact arrangement of the spatial components, which reduces dispensing unit's dimensions.

Figure 27A:
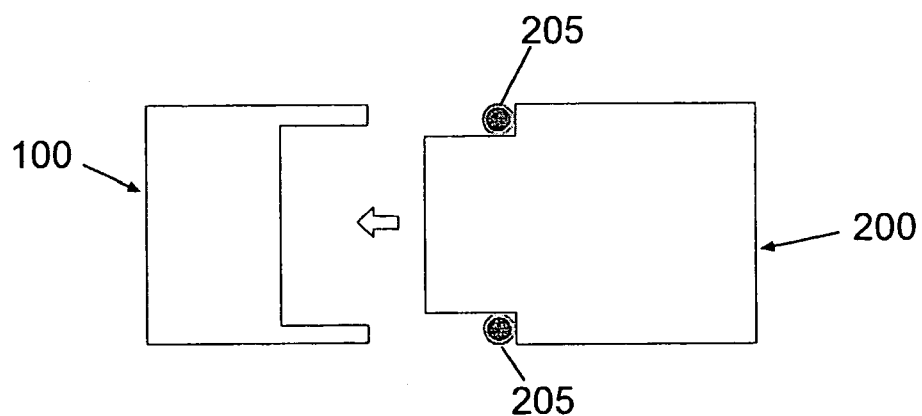
FIGS. 27a-b illustrate an exemplary sealing using a gasket e.g., 0-ring, upon connection of the reusable and disposable parts, according to some embodiments of the present invention.
Figure 27B:
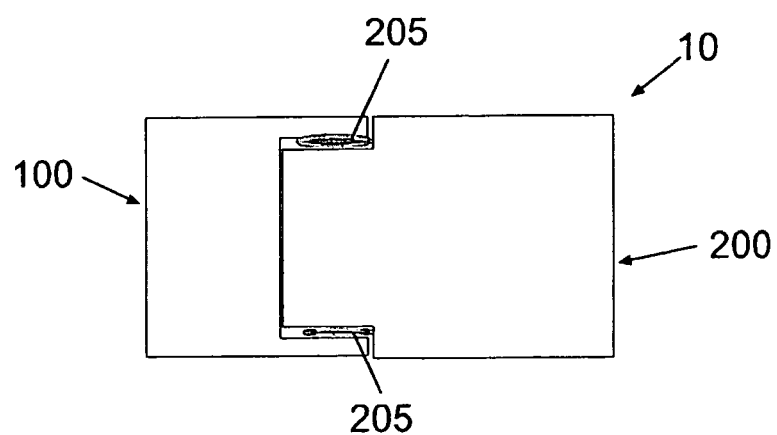
Figure 28A:
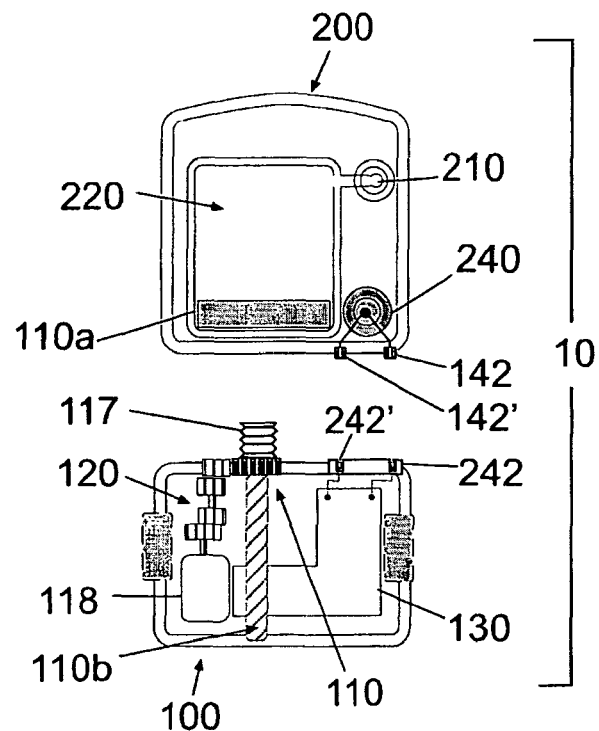
FIGS. 28a-b illustrate another exemplary sealing upon connection of the reusable and disposable parts, according to some embodiments of the present invention.
Figure 28B:
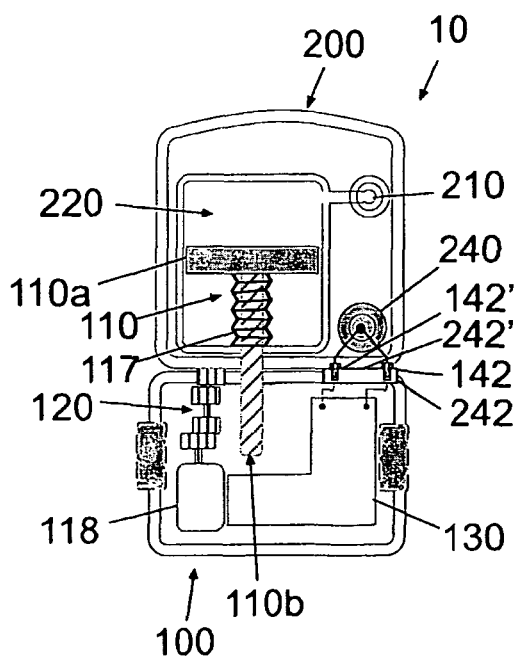

FIGS. 27a-28b show two embodiments of a sealing arrangement between the disposable part (200) and the reusable part (100) of the dispensing unit (10). In FIGS. 27a-b embodiment, sealing is achieved only after connection of reusable (100) and disposable (200) parts, while each part when it "stands alone" is not confined in a waterproof housing. In FIGS. 28a-b embodiment, each part has its own sealed housing.

FIG. 27a is a cross-sectional view of the reusable part (100) and the disposable part (200) prior to connection. In this embodiment, the disposable part (200) includes at least one gasket (205) (e.g., a rubber 0-ring) being attached to the housing of the disposable part (200). In some embodiments, the gasket(s) (205) can be attached to the reusable part (100) or can be attached to both parts. Once the reusable part (100) and the disposable part (200) are connected together, the gasket(s) (205) seal the parts together, thereby preventing damage to internal components, entry of moisture, contaminants, or other unwanted particles, as shown in FIG. 27b.

FIG. 28a shows the two "stand alone" parts each being sealed in a dedicated housing. The reusable part (100) contains two sharp battery connections (242) and (242') emerging outwardly including sharp ends and a folding accordion (117) for receiving the plunger rod (110b) and sealing thereof. The disposable part (200) contains two self-sealed septa (142) and (142') for sealing the battery connections. FIG. 28b shows the connected two parts. The battery connections (242) and (242') pierce the corresponding septa (142) and (142'), thereby establishing an electrical connection between the battery (240) (located in disposable part (200)), PCB (130) and electronic components (located in reusable part (100)). The plunger rod (110b) is sealingly covered by the accordion (117) and displaces the plunger head (110a).

FIGS. 29a-30b show other exemplary embodiments of the dispensing unit (10) having the disposable part (200) and the reusable part (100).

Figure 29A:
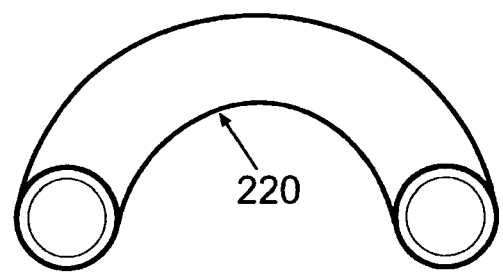
FIGS. 29a-d illustrate the dispensing unit having reusable and disposable parts configured as a half-torus, according to some embodiments of the present invention.
Figure 29B:
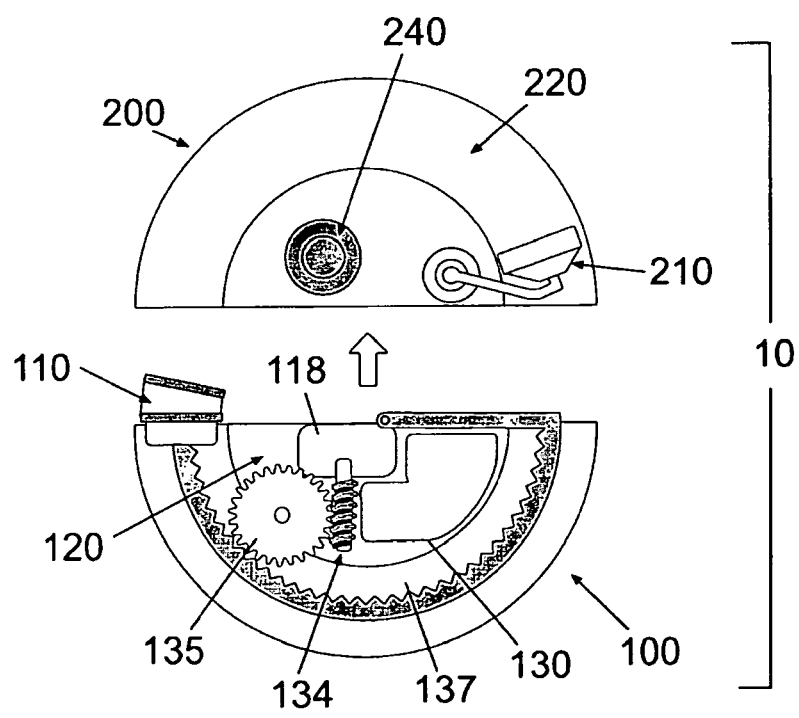
Figure 29C:
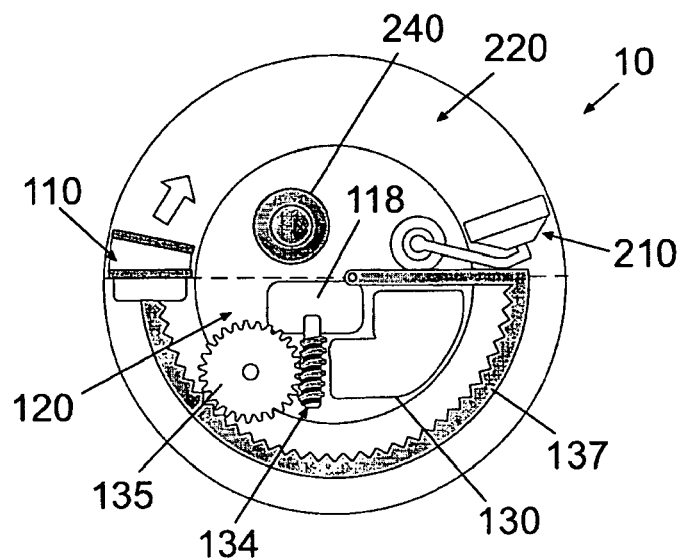
Figure 29D:
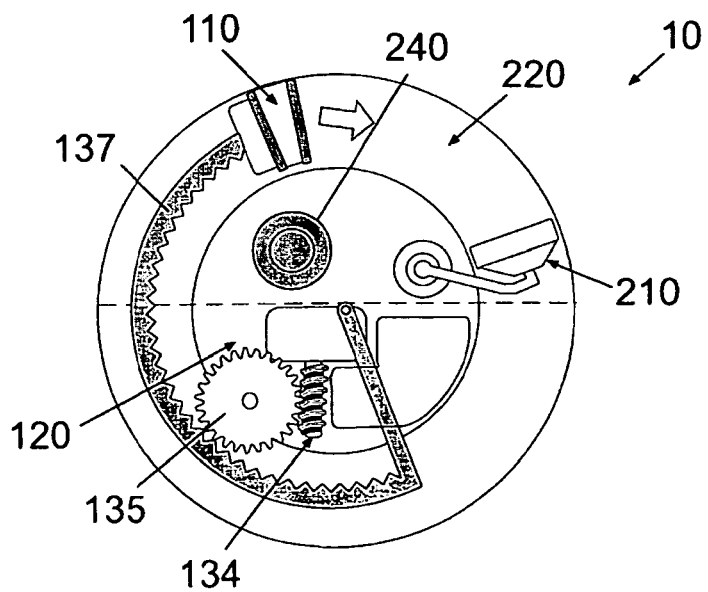

FIG. 29a shows a reservoir (220) configured as half a torus. A cross-section of the shown reservoir (220) can be elliptical, oval, multi-curved or any other desired cross-section. Reservoir's shape and cross-section dictates the configuration of other components (e.g., plunger), housing etc. FIGS. 29b-d show the implementation of the reservoir (220) shown in FIG. 29a.

FIG. 29b shows the two parts each configured as half of a torus. The disposable part (200) has a half-torus reservoir (220), battery (240) and outlet port (210). The reusable part (100) includes driving mechanism (120) (e.g., motor and gear), plunger (110), PCB (130) and other relatively expensive components, e.g., occlusion sensor (not shown). The driving mechanism (120) further includes a motor (118), a worm (134), a secondary gear (135), and a circular gear (137). The circular gear (137) is pivotally coupled to the housing of the reusable part (100). The motor (118) rotates the worm (134), which in turn rotates the secondary gear (135). As the gear (135) rotates, its ratchet teeth interact with the teeth of the circular gear (137), thereby forcing rotation of the gear (137) about its pivotal connection to the reusable part (100). As the plunger (110) is coupled to the gear (137), circular movement of the gear (137) causes the plunger (110) to be displaced inside the reservoir (220). Since the gear (137) is circular and the reservoir (220) is also circular, the gear (137) is displaced along the curvature of the reservoir (220), thereby displacing fluid toward the outlet port (210), as shown in FIGS. 29c-d. Reverse motion of the gear (135) allows reverse movement of the gear (137) along with the plunger (110) away from the reservoir (220).

Figure 30A:
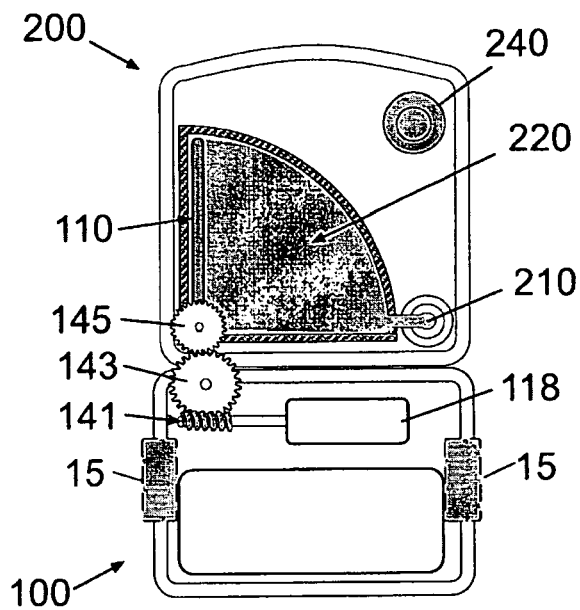
FIGS. 30a-b illustrate the dispensing unit having reusable and disposable parts where reservoir is configured as a sector, according to some embodiments of the present invention.
Figure 30B:
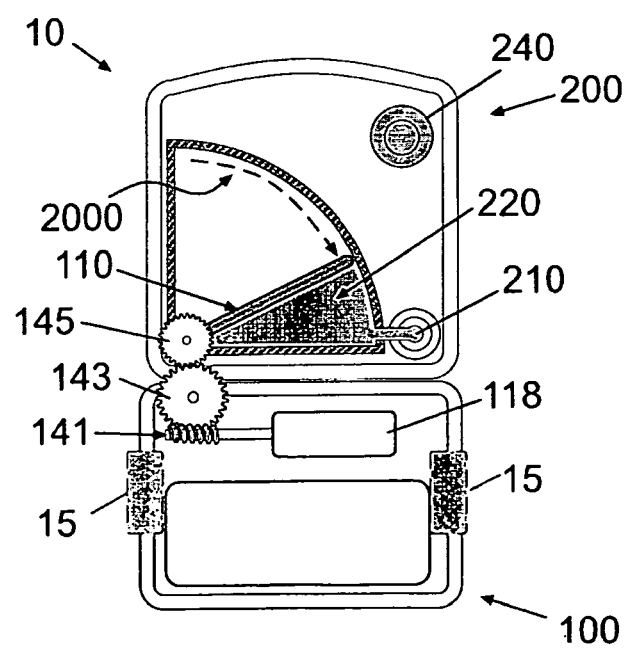

FIGS. 30a-b shows another exemplary embodiment of the dispensing unit (10), where the disposable part (200) includes the reservoir (220) configured as a sector (e.g., quarter of a circle), the plunger (110) configured in a similar way as a windshield wiper, the battery (240) and the outlet port (210). The reusable part (100) includes the driving mechanism (120), the electronics (130), the buttons (15) and other additional components (e.g., occlusion sensor (not shown)). The driving mechanism includes the motor (118), a worm (141), a first gear (143), and a secondary gear (145). The motor (118) rotates the worm (141), which causes rotation of the first gear (143) through interaction of the worm (141) with the ratchet teeth of the first gear (143). The first gear (143), in turn, causes rotation of the second gear (145) via interaction of the gears' teeth. The plunger (110) is coupled to the second gear (145) and rotates with the rotation of the gear (145). Since the plunger (110) is configured as a rod, it pushes the liquid disposed inside the reservoir (220) toward the outlet port (210). FIG. 30b shows the dispensing unit (10) in operation mode while the plunger (110) moves along the direction (2000) urging fluid from the reservoir (220) towards the outlet port (210).

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, presently unclaimed inventions are also contemplated. The inventors reserve the right to pursue such inventions in later claims.

All of the patents and pending patent applications referenced in this application are hereby incorporated by reference herein in their entireties.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An apparatus for delivering a therapeutic fluid into a body of a patient, comprising:
   a dispensing unit with:
      a reusable part;
      a disposable part comprising a housing with an outlet port, a reservoir for the therapeutic fluid and a connecting lumen that is part of and extends from the outlet port and which is in fluid communication directly with the reservoir;
      a plunger having a plunger head and a plunger rod for displacing the therapeutic fluid from the reservoir to the outlet port;
      a driving mechanism; and
      an electronic component including at least a controller for controlling at least the operation of the driving mechanism, and
   a cradle with upper and bottom sides, wherein the bottom side is adherable to skin of the patient, and the dispensing unit is connectable to and disconnectable from the upper side of the cradle, wherein the cradle further comprises a tubular protrusion emerging upwardly from the upper side which defines a well therein, the outlet port being configured as a recess in the housing of the disposal part which is sized to accommodate the tubular protrusion of the cradle, and the connecting lumen is configured to pierce a septum provided in the well upon accommodation of the tubular protrusion of the cradle in the outlet port which simultaneously fluidically connects, via the connecting lumen, the reservoir to a cannula extending from the bottom side of the cradle.

2. The apparatus of claim 1 wherein the reservoir has a substantially flat cross-sectional profile with a shape selected from the group consisting of an oval, an ellipse, and a rectangle.

3. The apparatus of claim 1, wherein the disposable part comprises a cross-section of less than fifteen millimeters.

4. The apparatus of claim 1 wherein the reservoir is a part of a syringe fitted with the plunger, and the plunger comprises a displaceable piston plunger.

5. The apparatus of claim 1 wherein the outlet port is configured and dimensioned to fit to a drug glass bottle cork.

6. The apparatus of claim 1 wherein the outlet port is provided with a short connecting element having a sharp hollow tip for fluid communication between the reservoir and a bottle, which enables drug drawing from the bottle upon backward movement of the plunger while the bottle is positioned upside down.

7. The apparatus of claim 1 wherein the fluid is drawn from a container by pulling on a shaft of the plunger that creates a suction effect thereby drawing the fluid from the container.

8. The apparatus of claim 1 wherein the reservoir has either an elliptical or an oval cross-sectional configuration such that the reservoir has a profile comprising a thickness of about ten millimeters.

9. The apparatus of claim 1 wherein the reservoir contains a maximum of two cubic centimeters of fluid.

10. The apparatus of claim 1 wherein the housing is made at least partially from a transparent material to allow the patient to continuously monitor a level and/or a content of fluid in the reservoir.

11. The apparatus of claim 1 wherein the outlet port of the disposable part allows direct filling of the reservoir with the therapeutic fluid from a therapeutic fluid container connectable directly to the disposable part via the outlet port.

12. The apparatus of claim 1 further comprising a detachable auxiliary rod coupleable to the plunger head when the plunger rod is disconnected from the plunger head, for enabling the pulling of the plunger head outwardly within the reservoir.

13. The apparatus of claim 1, wherein the cradle further comprises anchoring latches disposed around a perimeter of the cradle to secure releasably the dispensing unit to the cradle.

14. The apparatus of claim 13, wherein the anchoring latches create a snap-fit locking arrangement between the latches and the dispensing unit.

15. The apparatus of claim 1 wherein a therapeutic fluid container is connectable directly to the disposable part via the outlet port to fluidically connect the reservoir to the container and wherein the plunger rod is configured to disconnect from the plunger head and be replaceable by a detachable auxiliary rod, the auxiliary rod being configured to couple directly to the plunger head for enabling the pulling of the plunger head outwardly within the reservoir to fill the reservoir with the therapeutic fluid from the container via the connecting lumen.

16. A method for delivering a therapeutic fluid into a body of a patient, comprising:
   providing an apparatus comprising:
      a dispensing unit which has:
         a reusable part;
         a disposable part comprising a housing with an outlet port, a reservoir for the therapeutic fluid and a connecting lumen that is part of and extends from the outlet port and which is in fluid communication directly with the reservoir;
         a plunger having a plunger head and a plunger rod for displacing the therapeutic fluid from the reservoir to the outlet port;
         a driving mechanism; and
         an electronic component including at least a controller for controlling at least the operation of the driving mechanism; and
      a cradle with upper and bottom sides, wherein the bottom side is adherable to skin of the patient, and the dispensing unit is connectable to and disconnectable from the upper side of the cradle, wherein the cradle further comprises a tubular protrusion emerging upwardly from the upper side which defines a well therein, the outlet port being configured as a recess in the housing of the disposal part which is sized to accommodate the tubular protrusion of the cradle, and the connecting lumen is configured to pierce a septum provided in the well upon accommodation of the tubular protrusion of the cradle in the outlet port which simultaneously fluidically connects, via the connecting lumen, the reservoir to a cannula extending from the bottom side of the cradle;

piercing a septum of a container with a connecting element of the reservoir; and pulling on a shaft of the plunger, creating a suction effect thereby drawing the therapeutic fluid from the container.

17. The method of claim 16 further comprising disconnecting the plunger rod from the plunger head and coupling an auxiliary rod to the plunger head, followed by pulling of the plunger head outwardly within the reservoir.

18. The method of claim 16 further comprising connecting the reusable part to the disposable part, and then connecting the dispending unit to the cradle.

19. The method of claim 17 wherein pulling of the plunger head outwardly within the reservoir via the auxiliary rod fills the reservoir with the therapeutic fluid from the container via the connecting lumen.

\* \* \* \* \*